US011298562B2

(12) United States Patent
Tankovich

(10) Patent No.: US 11,298,562 B2
(45) Date of Patent: Apr. 12, 2022

(54) ATTACHABLE TIP FOR ULTRASOUND HAND PIECE

(71) Applicant: Nikolai Tankovich, San Diego, CA (US)

(72) Inventor: Nikolai Tankovich, San Diego, CA (US)

( * ) Notice: Subject to any disclaimer, the term of this patent is extended or adjusted under 35 U.S.C. 154(b) by 20 days.

(21) Appl. No.: 16/876,088

(22) Filed: May 17, 2020

(65) Prior Publication Data

US 2020/0346029 A1 Nov. 5, 2020

Related U.S. Application Data

(62) Division of application No. 16/503,299, filed on Jul. 3, 2019, now Pat. No. 10,702,703, which is a division of application No. 15/408,415, filed on Jan. 17, 2017, now Pat. No. 10,420,955.

(60) Provisional application No. 62/280,075, filed on Jan. 18, 2016.

(51) Int. Cl.
| | | |
|---|---|---|
| *A61M 35/00* | (2006.01) | |
| *A61N 5/06* | (2006.01) | |
| *A61N 1/32* | (2006.01) | |
| *A61M 37/00* | (2006.01) | |
| *A61M 5/19* | (2006.01) | |
| *A61B 18/20* | (2006.01) | |
| *A61B 18/00* | (2006.01) | |
| *A61N 5/00* | (2006.01) | |
| *A61N 7/00* | (2006.01) | |
| *A61N 5/067* | (2006.01) | |

(52) U.S. Cl.
CPC ............ *A61N 5/062* (2013.01); *A61B 18/203* (2013.01); *A61M 5/19* (2013.01); *A61M 35/003* (2013.01); *A61M 37/0092* (2013.01); *A61N 1/327* (2013.01); *A61N 5/0616* (2013.01); *A61B 2018/00029* (2013.01); *A61B 2018/0047* (2013.01); *A61B 2018/0091* (2013.01); *A61B 2018/208* (2013.01); *A61M 2037/0007* (2013.01); *A61N 5/067* (2021.08); *A61N 2005/007* (2013.01); *A61N 2005/0644* (2013.01); *A61N 2007/0034* (2013.01)

(58) Field of Classification Search
CPC ...... A61N 5/062; A61N 1/327; A61N 5/0616; A61N 2007/0034; A61N 2005/0644; A61N 2005/067; A61N 2005/007; A61B 18/203; A61B 2018/208; A61B 2018/0047; A61B 2018/00029; A61B 2018/0091; A61M 5/19; A61M 37/0092; A61M 35/003; A61M 2037/0007

See application file for complete search history.

(56) References Cited

U.S. PATENT DOCUMENTS

| | | |
|---|---|---|
| 1,890,599 A | 12/1935 | Cobello |
| 5,415,652 A | 5/1995 | Mueller |
| 5,616,141 A | 4/1997 | Cipolla |
| 6,149,645 A | 11/2000 | Tobinick |

(Continued)

*Primary Examiner* — Tatyana Zalukaeva
*Assistant Examiner* — Jessica R Arble
(74) *Attorney, Agent, or Firm* — TMB Law; Timothy M. Brown

(57) ABSTRACT

A system for the surface and subsurface delivery of therapeutic and cosmetic agents. The system includes a disposable attachable tip that can be pre-filled with medications or cosmetics and attached to hand pieces including electromagnetic and mechanical energy hand piece devices.

11 Claims, 20 Drawing Sheets

(56) References Cited

U.S. PATENT DOCUMENTS

| | | | |
|---|---|---|---|
| 6,387,089 B1 | 5/2002 | Kreindel | |
| 6,569,156 B1 | 5/2003 | Tankovich | |
| 7,306,459 B1 | 12/2007 | Williams | |
| 9,861,442 B2 | 1/2018 | Tankovich | |
| 10,420,955 B2 | 10/2019 | Tankovich | |
| 10,702,703 B2 | 7/2020 | Tankovich | |
| 2002/0183727 A1 | 12/2002 | Daikuzono | |
| 2003/0004499 A1 | 1/2003 | McDaniel | |
| 2003/0208159 A1* | 11/2003 | Ignon | A61B 17/545 604/140 |
| 2004/0030325 A1 | 2/2004 | Cahir | |
| 2005/0137584 A1 | 6/2005 | Lemchen | |
| 2005/0222565 A1 | 10/2005 | Manstein | |
| 2006/0074468 A1 | 4/2006 | Neev | |
| 2006/0093424 A1 | 5/2006 | Tsaur | |
| 2007/0225779 A1* | 9/2007 | Hantash | A61L 27/3895 607/89 |
| 2007/0253761 A1 | 11/2007 | May | |
| 2008/0255549 A1 | 10/2008 | Rose | |
| 2009/0130622 A1 | 5/2009 | Bollinger | |
| 2011/0040235 A1 | 2/2011 | Castel | |
| 2011/0160712 A1 | 6/2011 | Tankovich | |
| 2013/0197550 A1* | 8/2013 | Dietz | A61N 7/00 606/169 |
| 2014/0073996 A1 | 3/2014 | Jaguan | |
| 2014/0243794 A1* | 8/2014 | Halskov | A61K 9/14 604/514 |
| 2015/0257828 A1 | 9/2015 | Tankovich | |
| 2016/0101273 A1* | 4/2016 | Unger | A61N 1/30 604/22 |
| 2017/0056636 A1* | 3/2017 | Shadduck | A61M 1/0084 |
| 2017/0225010 A1 | 8/2017 | Tankovich | |
| 2018/0147012 A1 | 5/2018 | Tankovich | |
| 2020/0030625 A1 | 1/2020 | Tankovich | |

\* cited by examiner

ULTRA SOUND DIAGNOSTIC TIP

ULTRASOUND MEDICAL/COSMETIC TIP

MULTI-SUBSTANCE TIP
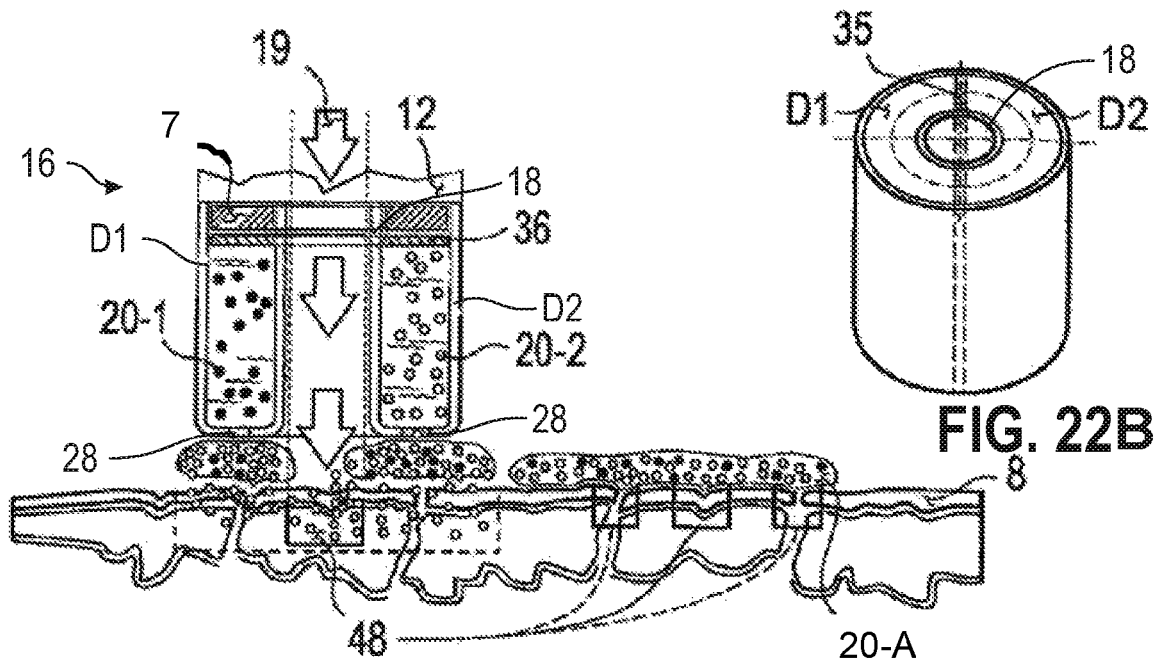
FIG. 22A
FIG. 22B
"EXTEMPORE" MIXTURE TIP
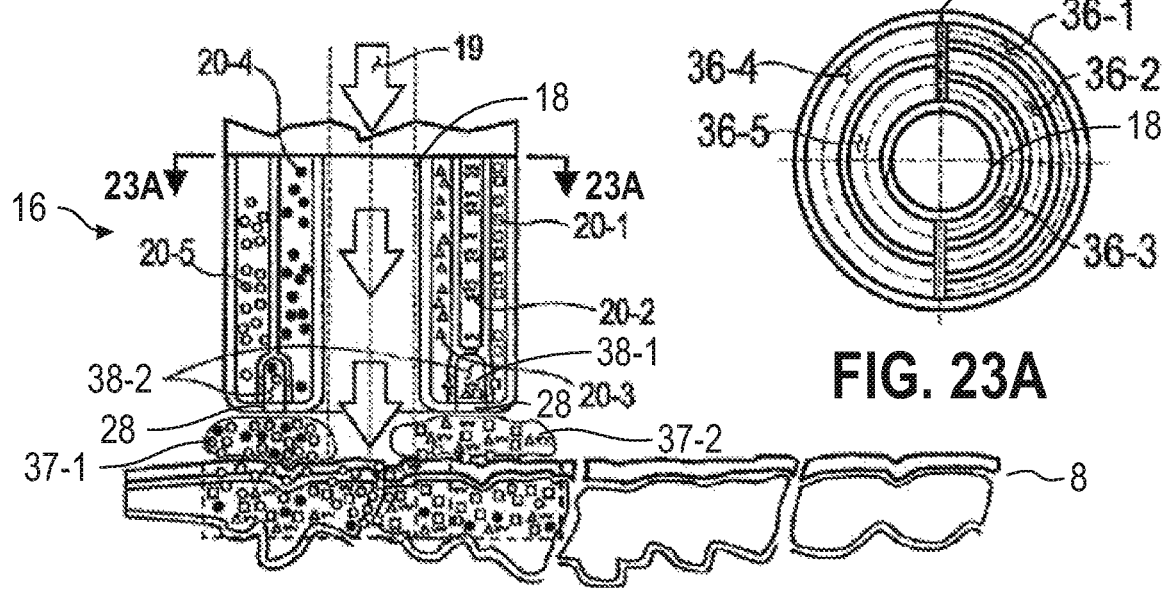
FIG. 23A
FIG. 23

COOLING AND CARRING TIP

ATTACHABLE TIP FOR ULTRASOUND HAND PIECE

RELATED APPLICATIONS

This application is a divisional of application Ser. No. 16/503,299 filed Jul. 3, 2019, which is a divisional of application Ser. No. 15/408,415 filed Jan. 17, 2017, which claims the benefit of Provisional Application No. 62/280,075 filed Jan. 18, 2016. The contents of these applications are incorporated herein by reference in their entirety for all purposes.

FIELD OF THE INVENTION

The invention generally relates to attachable tips for use with hand pieces of electromagnetic and mechanical energy delivery devices for medical and cosmetic use. More particularly, the invention relates to attachable tips for delivering therapeutic and cosmetic agents in conjunction with hand pieces of electromagnetic and mechanical energy delivery devices.

BACKGROUND OF THE INVENTION

A variety of different compounds, compositions, drugs, skin care products, and cosmetics are in use today. Moreover, these agents have been used following the application of laser therapy and mechanical abrasion as a means for alleviating pain and preventing infection. However, the use of mechanical and electromagnetic energy has not been applied to effect the delivery of therapeutic and cosmetic agents simultaneously with the application of mechanical and electromagnetic energy.

Thus, a need exists for devices and methods that permit the application of therapeutic and cosmetic agents simultaneously with the delivery of mechanical and electromagnetic energy to the skin and its associated structures.

SUMMARY OF THE INVENTION

The present invention meets the needs in the art by providing attachable tips for hand pieces that generate electromagnetic and mechanic energy for application to the surface of the skin. The attachable tips of the invention can deliver a precise amount of drug, medication, biologic, gene, compound or a composition of several substances, coolant, cosmetics pre-loaded in it or supplied to it.

In one aspect, the invention provides a system comprising a laser hand piece and an attachable tip. The system includes components for producing a continuous or pulse energy beam, components for delivering substances to the damaged region of skin. The system can be designed to control and utilize a laser beam for partial perforation or vaporization of small volume of skin tissue and using a disposable or refillable attachable tip for a laser hand piece to deliver a substance which is applied prior, simultaneously or with some delay to produce a combination of laser action with the action of an agent at the same time. In some embodiments, a laser beam is delivered to produce on the skin damage using a scanning system or optical system to produce plurality of laser beams. The system can comprise a topical substance delivery attachable tip having one or more applicators with one or more agents delivered from individual applicators. The agent can be a medication, skin care, cosmetics, dye etc.

In one aspect, the invention provides a topical delivery attachable tip that can be used with a skin electroporation system for delivering topical agents while the skin is damaged by electric energy.

In one aspect, the invention provides an attachable tip for a laser hand piece that is designed to deliver skin surface cooling. The surface cooling can be provided by a heat absorbing agent. The heat absorbing agent can be a cooling gel delivered at a temperature of between about 1° C. and room temperature (e.g. 25° C.).

In one aspect, a topical delivery attachable tip can be combined with any laser hand piece of existing medical, aesthetic and cosmetic lasers.

In one aspect, the invention provides a system comprising an attachable tip as disclosed herein, and a hand piece as disclosed herein.

BRIEF DESCRIPTION OF THE DRAWINGS

FIG. 22A shows a multi-chamber attachable tip.

FIG. 22B shows a perspective view of the attachable tip of FIG. 22A.

FIG. 23 shows a multi-chamber attachable tip.

FIG. 23A shows a cross-sectional view of the multi-chamber attachable tip of FIG. 23.

DETAILED DESCRIPTION

The invention generally relates to attachable tips for use with hand pieces that deliver electromagnetic or mechanical energy to the skin. More particularly, the invention relates to attachable tips for delivering therapeutic and cosmetic agents to the skin in conjunction with hand pieces that apply electromagnetic and mechanical energy to the skin.

As used herein, the term "hand piece" refers to a device that is capable of delivering mechanical and/or electromagnetic energy to the skin of a subject. Hand pieces include, but are not limited to, devices capable of delivering one or more of: laser energy; intensive pulse light (IPL) energy; ultrasound energy; radio frequency (RF) energy; microwave energy; light emitting diode energy; x-rays; ionizing radiation; and electron beams.

Figure 1:
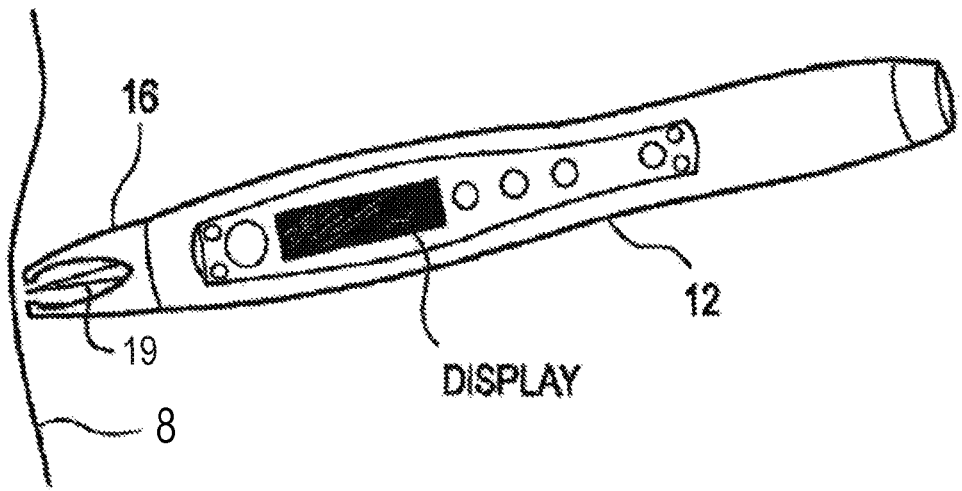
FIG. 1 shows an embodiment of a laser hand piece and attachable tip.

Hand pieces for use with the invention can be stand-alone devices that are not connected to any remote energy source and/or central control or processing unit. A non-limiting example of a stand-alone device is a laser hand piece, such as the device depicted in FIG. 1. Hand pieces can be powered by a battery or can plug in to a remote power source.

As used herein, the term "agent" refers to one or more substances that produce a desired biological, pharmacological, physiological and/or cosmetic effect in the subject to which the substance is administered.

FIGS. 1 through 5 show features of some embodiments of the present invention. The embodiment shown in FIG. 1 includes laser hand piece 12, attachable tip 16 and laser beam 19 emitting from hand piece 12 onto the surface of the skin 8. Attachable tip 16 can function as a standoff for optimal focusing of laser beam 19 onto the surface of the skin. Attachable tip 16 can contain one or more chambers as disclosed herein for containing an agent thereby permitting attachable tip 16 to function as an applicator that permits an agent to be applied to the skin simultaneously with the application of a laser beam. Attachable tips for use with the embodiments depicted in FIGS. 1 and 5 can assume the configurations depicted in FIGS. 4A-4C. The hand piece can be battery operated. The hand piece can have the functionality depicted in FIG. 2.

Figure 6:
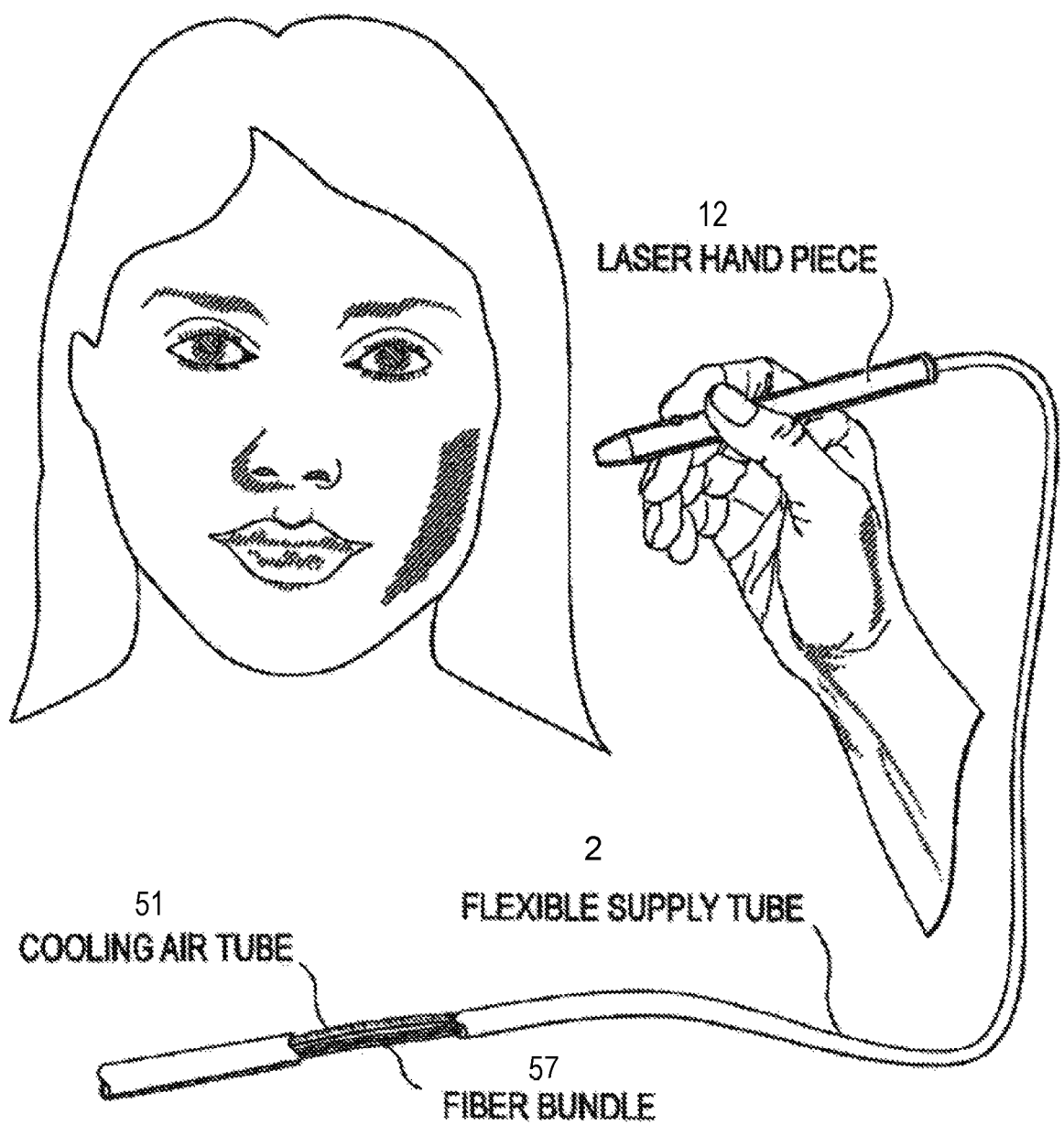
FIG. 6 shows a laser hand piece being applied to a patient.

FIG. 6 shows an embodiment of the inventive device having laser hand piece 12 and flexible supply tube 2. Flexible supply tube 2 can comprise fiber bundle 57 containing fibers and cooling air tube 51.

Figure 2:
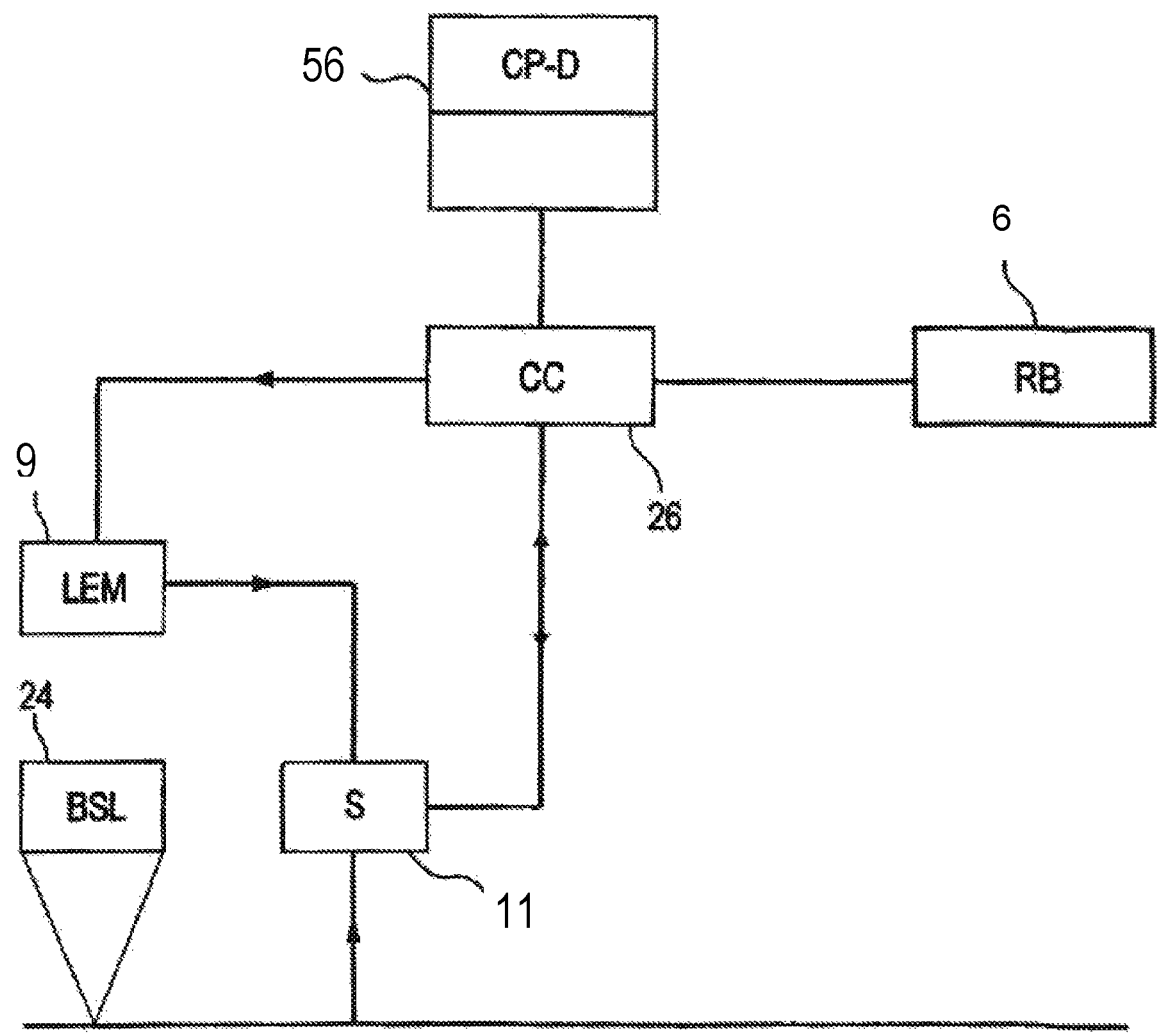
FIG. 2 shows a block diagram of a battery operated laser hand piece.
Figure 4A:
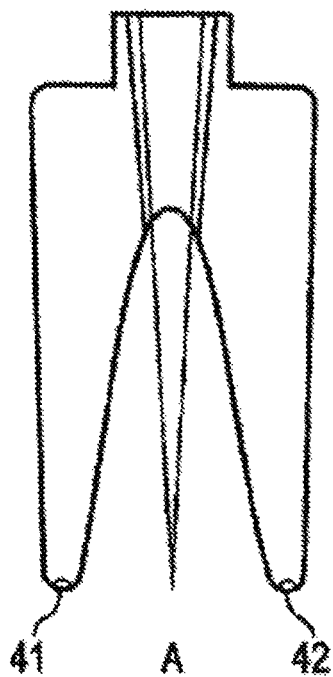
FIG. 4A shows an embodiment of an attachable tip with multiple applicators.
Figure 4B:
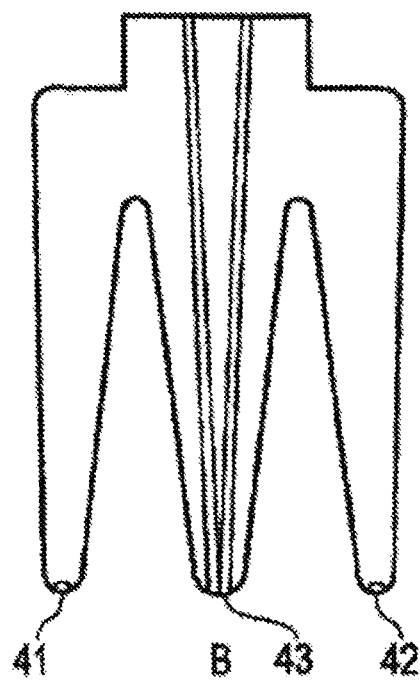
FIG. 4B shows a further embodiment of an attachable tip with multiple applicators.
Figure 4C:
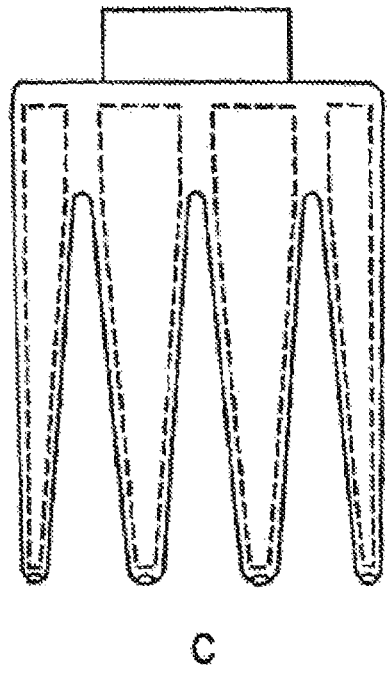
FIG. 4C shows a further embodiment of an attachable tip with multiple applicators.
Figure 7:
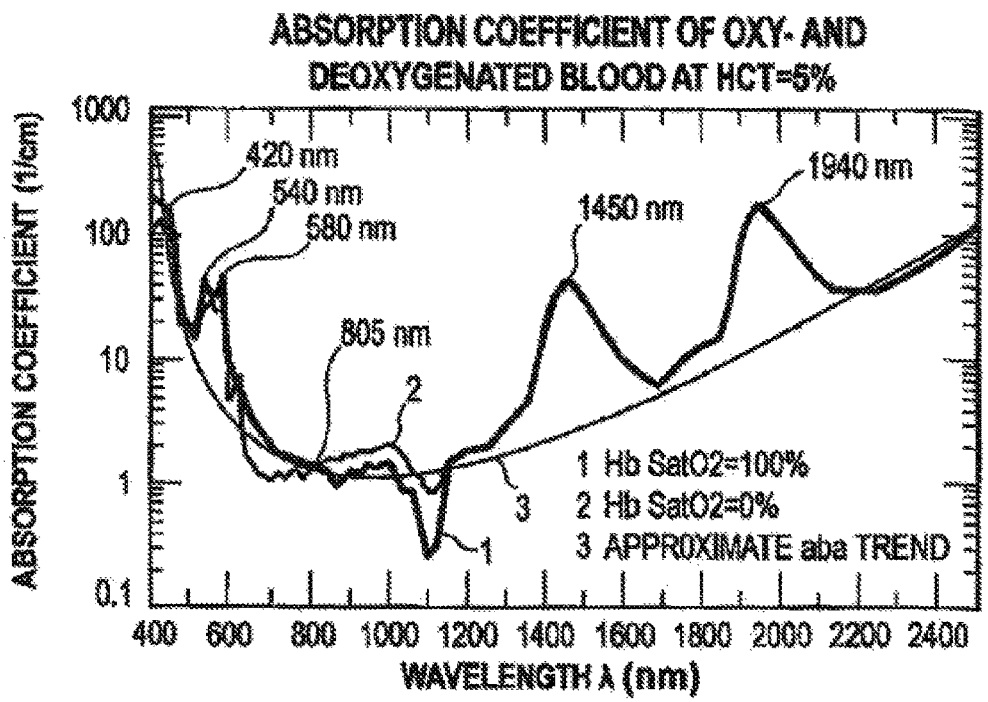
FIG. 7 is a graph showing absorption coefficients in blood.
Figure 8:
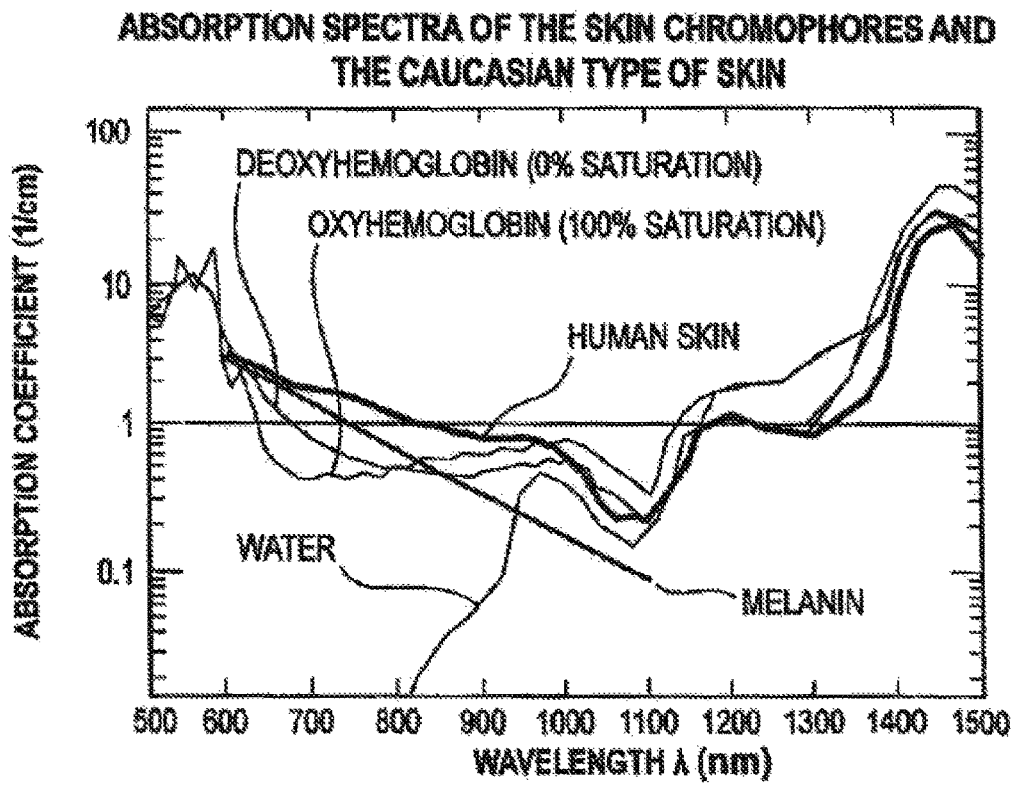
FIG. 8 is a graph showing absorption coefficients in skin.
Figure 9:
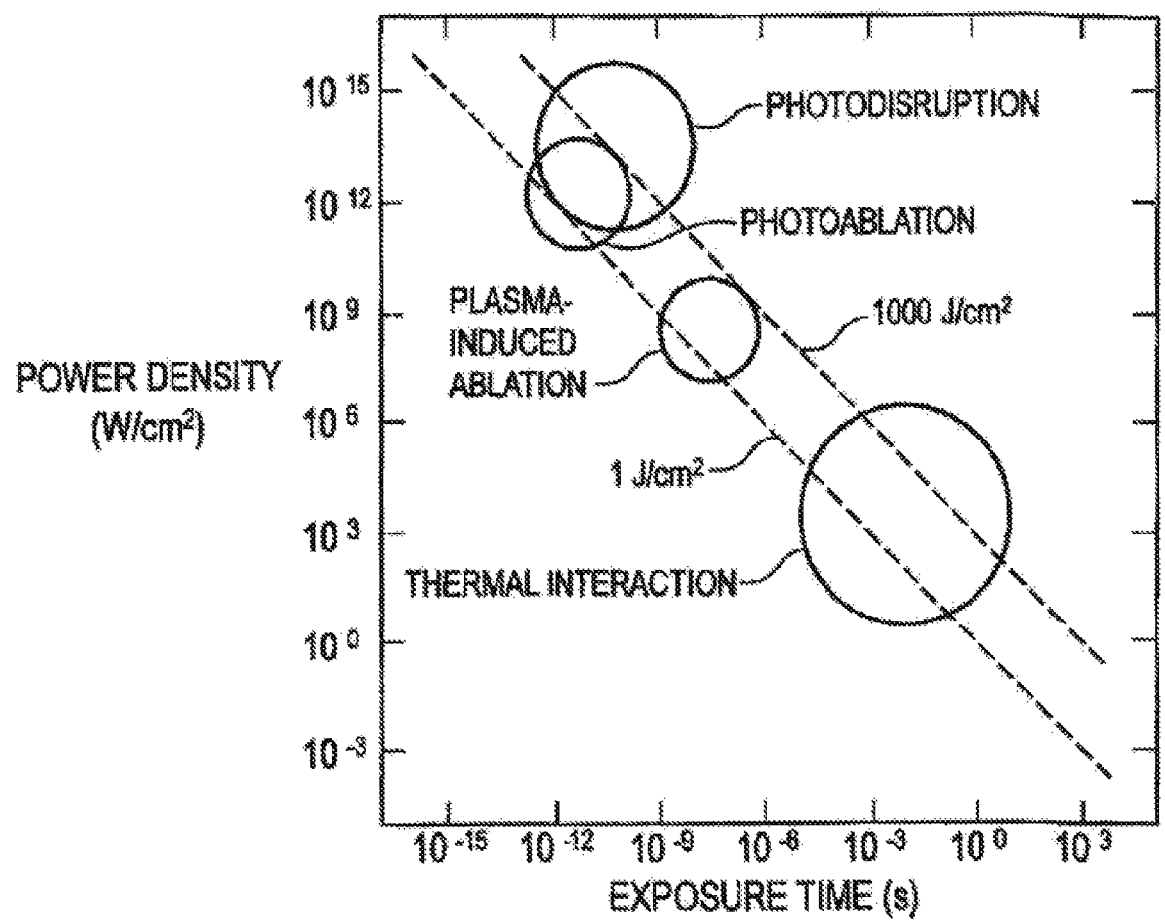
FIG. 9 is a diagram of laser-tissue interactions.

FIG. 2 shows the block diagram of an embodiment of a laser hand piece comprising a light energy emitting module 9, beam shaping lenses 24, control circuit 26, re-chargeable battery 6, sensors 11 and control panel 56 having a display. The light source can be a laser diode. The wavelength of the laser diode can be in the range of 1930 nm. The laser wavelength can be one or more of those depicted in FIGS. 7 and 8. The laser output can be laser pulses. The energy of the pulses and their repetition rate can be set at control panel 56 and displayed at the screen. The pulses can be one or more of those depicted in FIG. 9. The laser beam can be focused by beam shaping lenses 24 in a small spot at a distance of a length of that corresponds to the standoff of the attachable tip. Unless provided otherwise by the context of their description and/or function, the hand pieces disclosed in this specification which incorporate a laser can have the functionality described in FIG. 2, as well as the wavelengths and pulse intensity disclosed in FIGS. 7-9.

Figure 3:
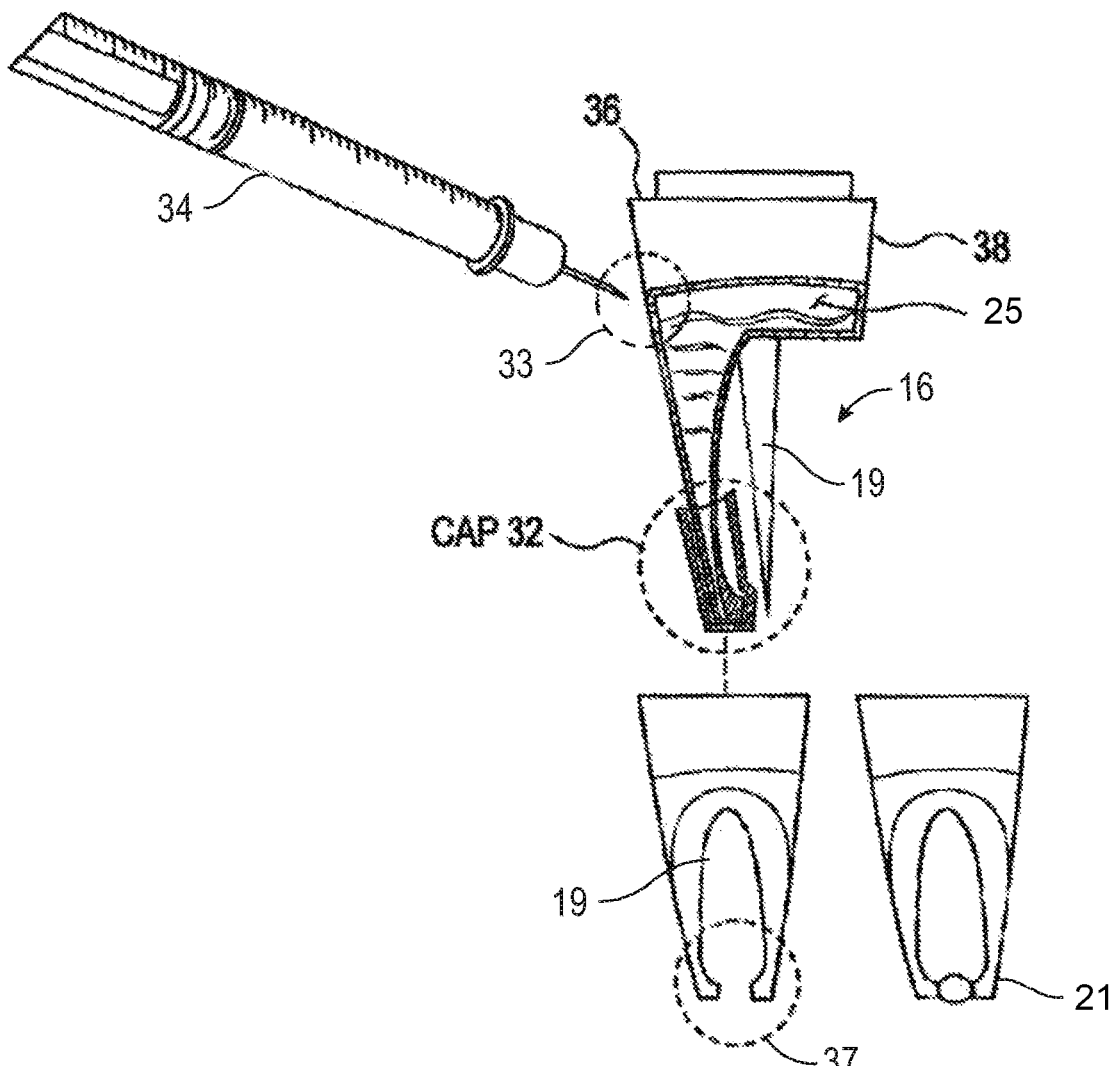
FIG. 3 shows the design of an attachable tip.

FIG. 3 shows an embodiment of an attachable tip according to the invention. Attachable tip 16 is defined by housing 38. Housing 38 can be made of a medical grade plastic. Attachable tip 16 can be enclosed in a sterilized individual bag. Attachable tip 16 can have attachment surface 36 for interacting with a hand piece for attaching attachable tip 16 to the hand piece. Attachable tip 16 can have chamber 25. Chamber 25 can be pre-filled filled with one or more agents. Chamber 25 can have one or more agents introduced into it by injection by syringe 34 having a needle for piercing housing 38. Chamber 25 can be under vacuum so as to draw the agent(s) from syringe 34 into chamber 25. Syringe 34 can be used to load one or more agents into an empty chamber 25 or used to introduce an additional one or more agents into chamber 25 which is pre-loaded with one or more agents. The one or more agents loaded or prefilled into chamber 25 can be a liquid, gel, cream, solid or other form of medicated substance. Housing 38 can have port 33 for injection of one or more agents into chamber 25. Port 33 traverses the outer and inner walls of housing 38 to permit the injection of one or more agents into chamber 25. Such ports may be advantageous when housing 38 is constructed of a durable plastic incapable of being pierced by a needle. Attachable tip 16 can have application port 37 on the bottom surface that is coplanar with attachment surface 36. Attachable tip 16 can have an application port (not shown) on the lower surface that is adjacent to, and coplanar with laser beam 19. The application port(s) traverse housing 38 and place chamber 25 in fluid communication with the surface of the skin when the attachable tip is placed in contact with a subject to be treated. Attachable tip 16 can have cap 32 for covering the application ports and preventing the escape of agents from a loaded chamber 25. Before use, cap 32 on the bottom of attachable tip 16 is removed before or after attachable tip 16 is snapped to a hand piece. Attachable tip 16 can have roller ball applicator 21 for rolling one or more agents onto the surface of the skin of a subject. In practice, attachable tip 16 is snapped onto a hand piece by interaction between the hand piece and attachment surface 36. Chamber 25 can be prefilled with an agent and/or have one or more agents introduced to it by injection by syringe 34. Cap 32 is then removed from attachable tip 16 and attachable tip 16 is contacted with the skin of a subject. One or more agents are then permitted to escape the application port(s). In an alternative embodiment, the one or more agents escape from application port 37 and are distributed onto the surface of the skin of a subject by roller ball applicator 21. The one or more agents can be applied to the skin before, during and/or simultaneously with the application of laser beam 19. The fluid in the attachable tip could be slightly heated up with electrical heater or by energy split from laser light. Application of the agent can take place after laser beam 19 damages the skin. Laser beam 19 can be a wavelength of 1930 nm. Laser beam 19 can be laser pulses. Laser beam 19 can make small openings in the stratum corneum to permit one or more agents from chamber 25 to penetrate the skin. The agent can be a filler such as, for example, hyaluronic acid. The filler can occupy openings in the skin created by laser beam 19.

Figure 10:
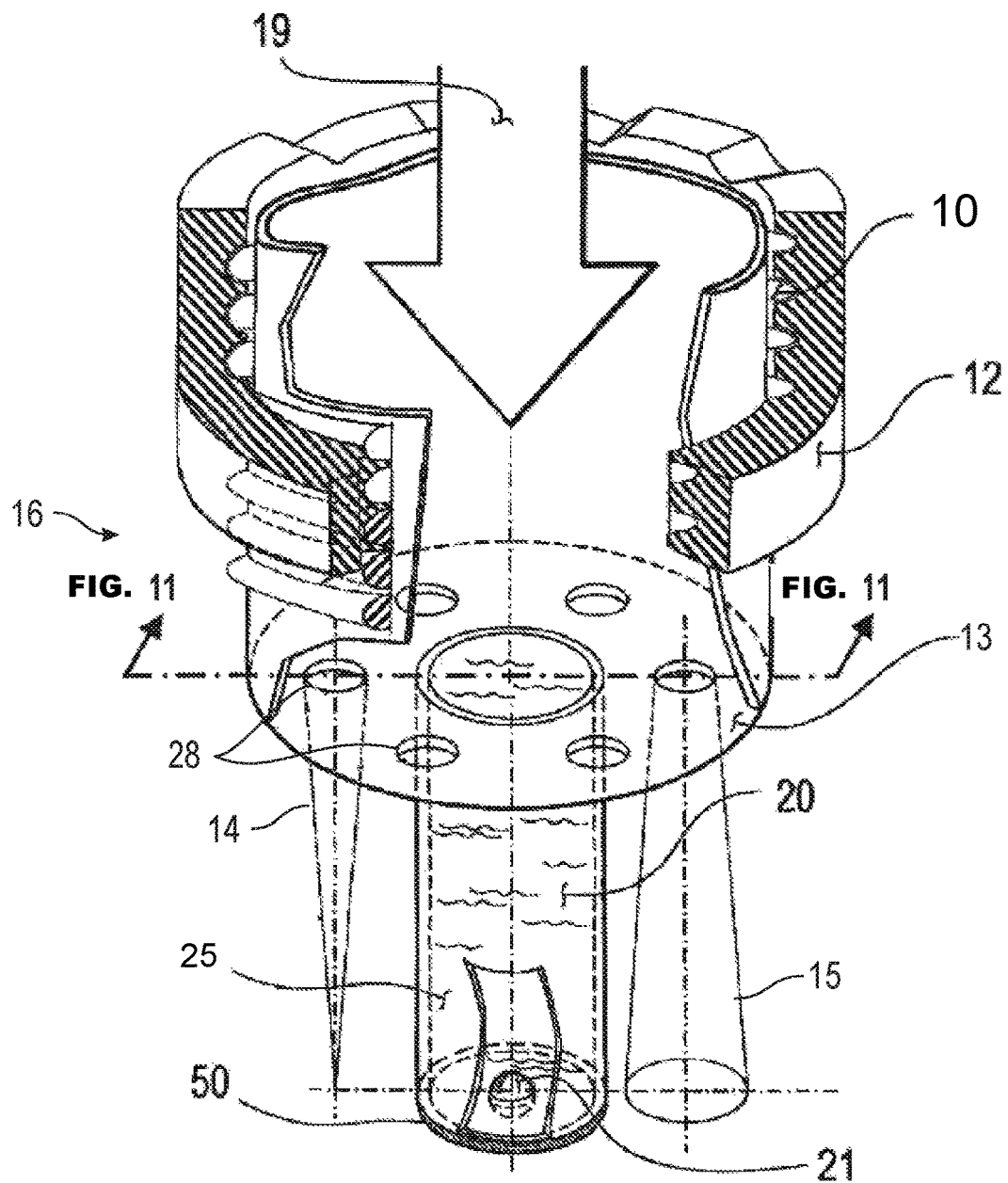
FIG. 10 shows an embodiment of an attachable tip for a laser hand piece.
Figure 11:
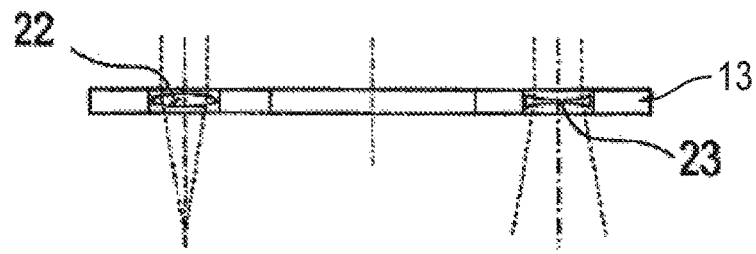
FIG. 11 shows lenses for use with an attachable tip for focusing or defocusing a laser beam.

FIGS. 10 and 11 illustrate an embodiment of an attachable tip for use with the invention. Attachable tip 16 has chamber 25 containing one or more agents 20. Attachable tip 16 can be connected to laser hand piece 12 by interaction of threads 10 with threads on hand piece 12. Attachable tip 16 has lens housing 13 having therein a plurality of windows 28 for transmission of laser beam 19 from laser hand piece 12. Each of windows 28 can contain focusing lens 22 or defocusing lenses 23. Focusing lens 22 focuses laser beam 19 onto a focal point as in focused laser beam 14. Defocusing lens 23 defocuses laser beam 19 into a diffuse laser pattern as in defocused laser beam 15. In operation, focused laser beam 14 and/or defocused laser beam 15 is projected onto the skin of a subject from windows 28. Laser beam 19 can remain collimated as well. Chamber 25 can be a cylinder that is defined by an inner wall. Chamber 25 can terminate in applicator surface 50 having therein a delivery window that traverses applicator surface 50 to permit chamber 25 to be in fluid communication with the skin of subject when attachable tip 16 is placed in contact with the skin of the subject. Applicator surface 50 can contain roller ball 21 for rolling agent 20 onto the skin of a subject. Chamber 25 can have a length that permits it to form a standoff for optimal focusing of laser beam 19 onto the surface of the skin of a subject. The length of chamber 25 can be coordinated with focusing lens 22 and/or defocusing lens 23 to achieve a desired degree of focus and/or defocusing of laser beam 19 on the skin of a subject. Laser beam 19 can be an Er:YAG solid state laser with a wavelength of 2,930 nm. The one or more agents can comprise an antracycline antibiotic.

Figure 12A:
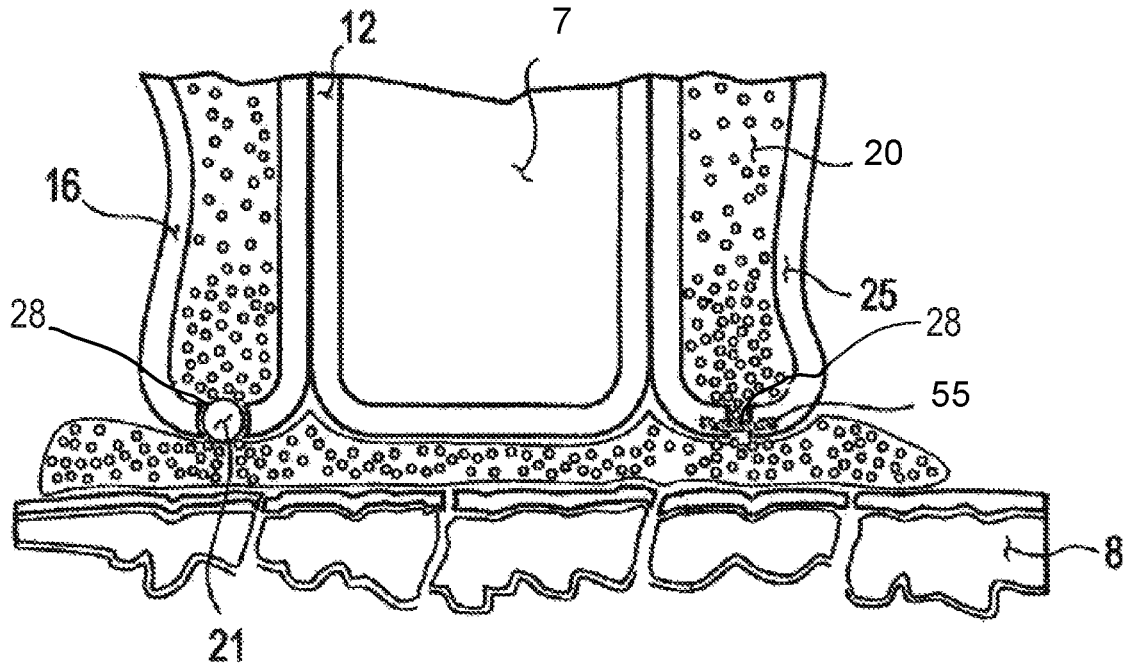
FIG. 12A shows an attachable tip for use with an ultrasound hand piece.
Figure 12B:
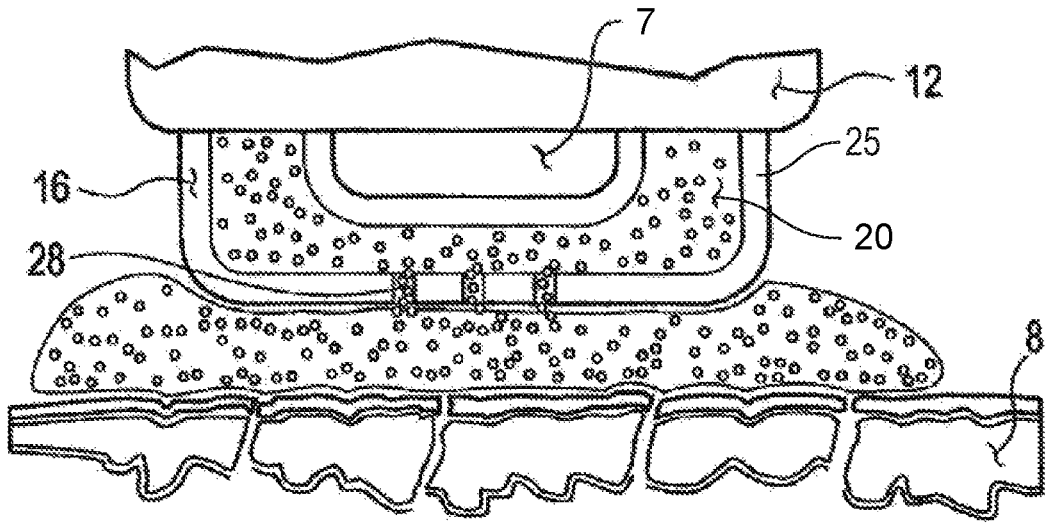
FIG. 12B shows a further embodiment of an attachable tip for use with an ultrasound hand piece.

FIGS. 12A and 12B show embodiments of an attachable tip for use with an ultrasound hand piece. Attachable tip 16 includes chamber 25 for containing agent 20. Attachable tip 16 has a circular cross-section (not shown) such that attachable tip 16 and chamber 25 encircles transducer 7 of hand piece 12. Attachable tip 16 is attached to hand piece 12 and transducer 7 by sliding onto transducer 7 as attachable tip 16 and chamber 25 form a cylindrical annulus. Attachable tip 16 has one or more windows 28 for placing chamber 25 in fluid communication with skin 8. Windows 28 traverse the wall of chamber 25. Windows 28 can be capped with a removable seal 55 to prevent agent 20 from escaping chamber 25. Windows 28 can have therein roller ball 21 for rolling agent 20 onto skin 8. Agent 20 can be selected from the group consisting of: a cooling gel; lubricant; ultrasound imaging agent; and a combination thereof. Attachable tip 16 can be formed from a flexible, squeezable material to permit attachable tip 16 to be squeezed so that agent 20 is forced through windows 28 and onto skin 8. In the embodiment depicted in FIG. 12B, application of ultrasound energy (shock waves) from transducer 7 functions to force agent 20 from chamber 25 onto skin 8.

Figure 13:
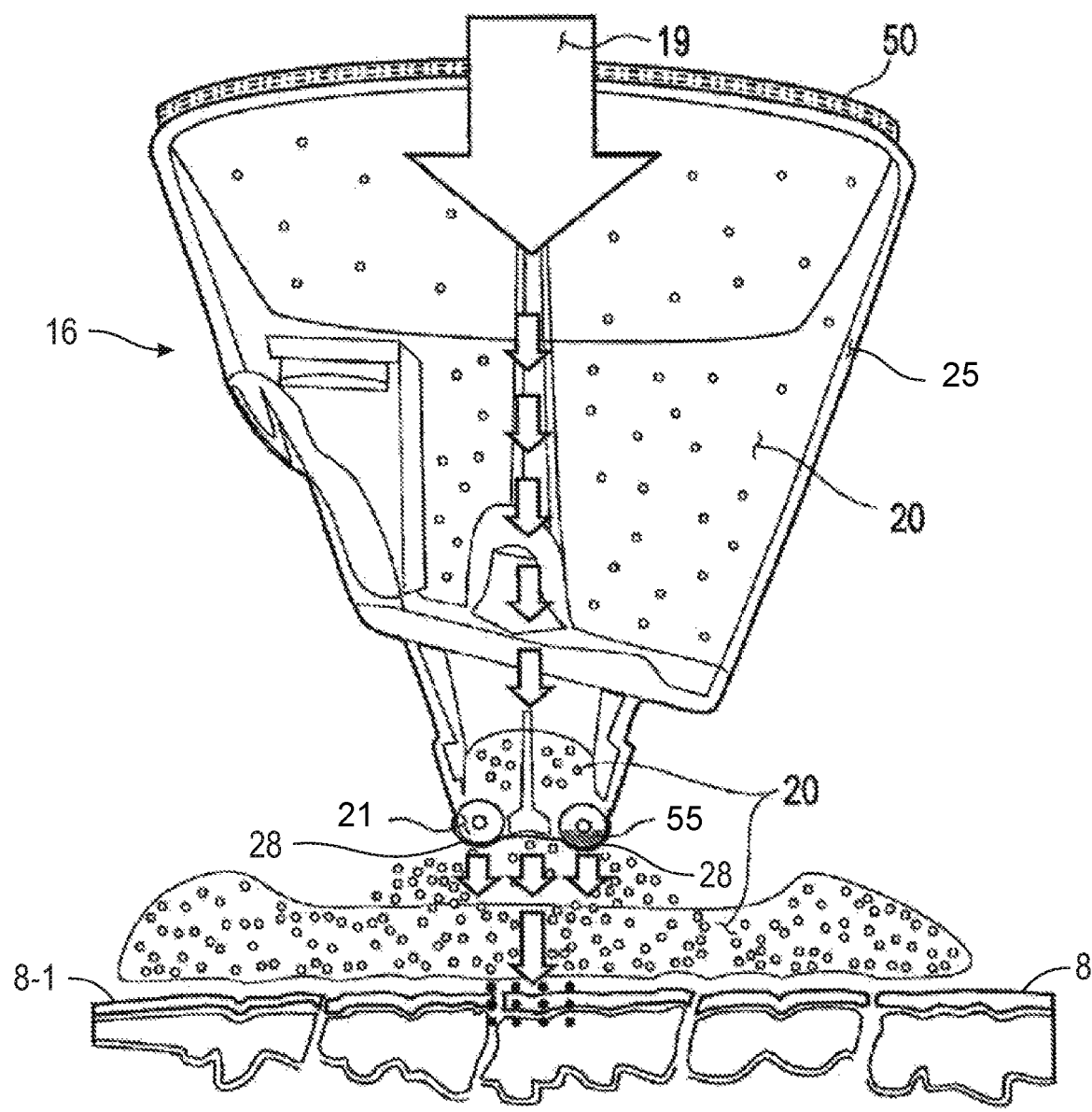
FIG. 13 shows an attachable tip in conjunction with a fractional laser hand piece.
Figure 14:
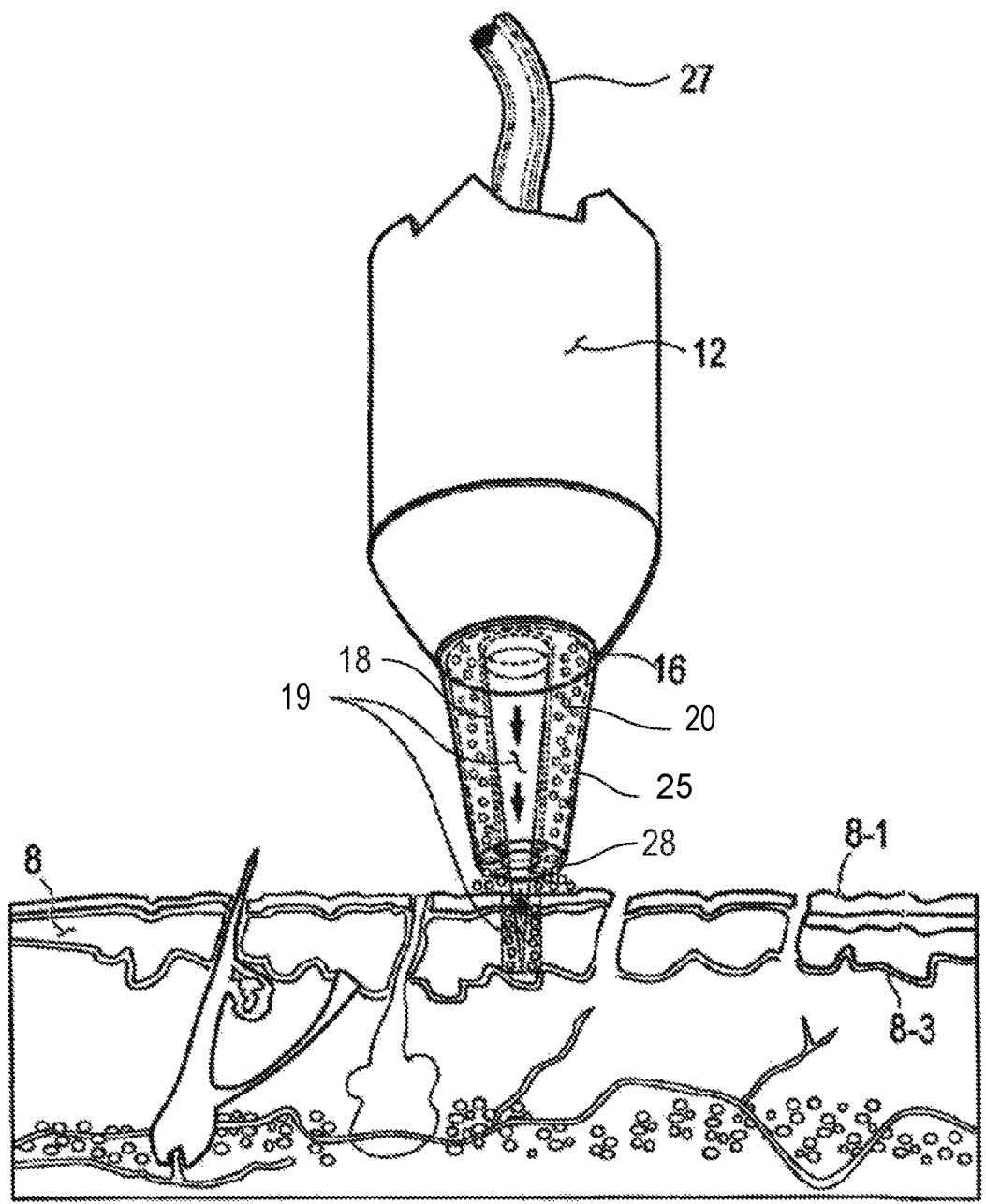
FIG. 14 shows an attachable tip with a fiber optic laser hand piece.
Figure 15:
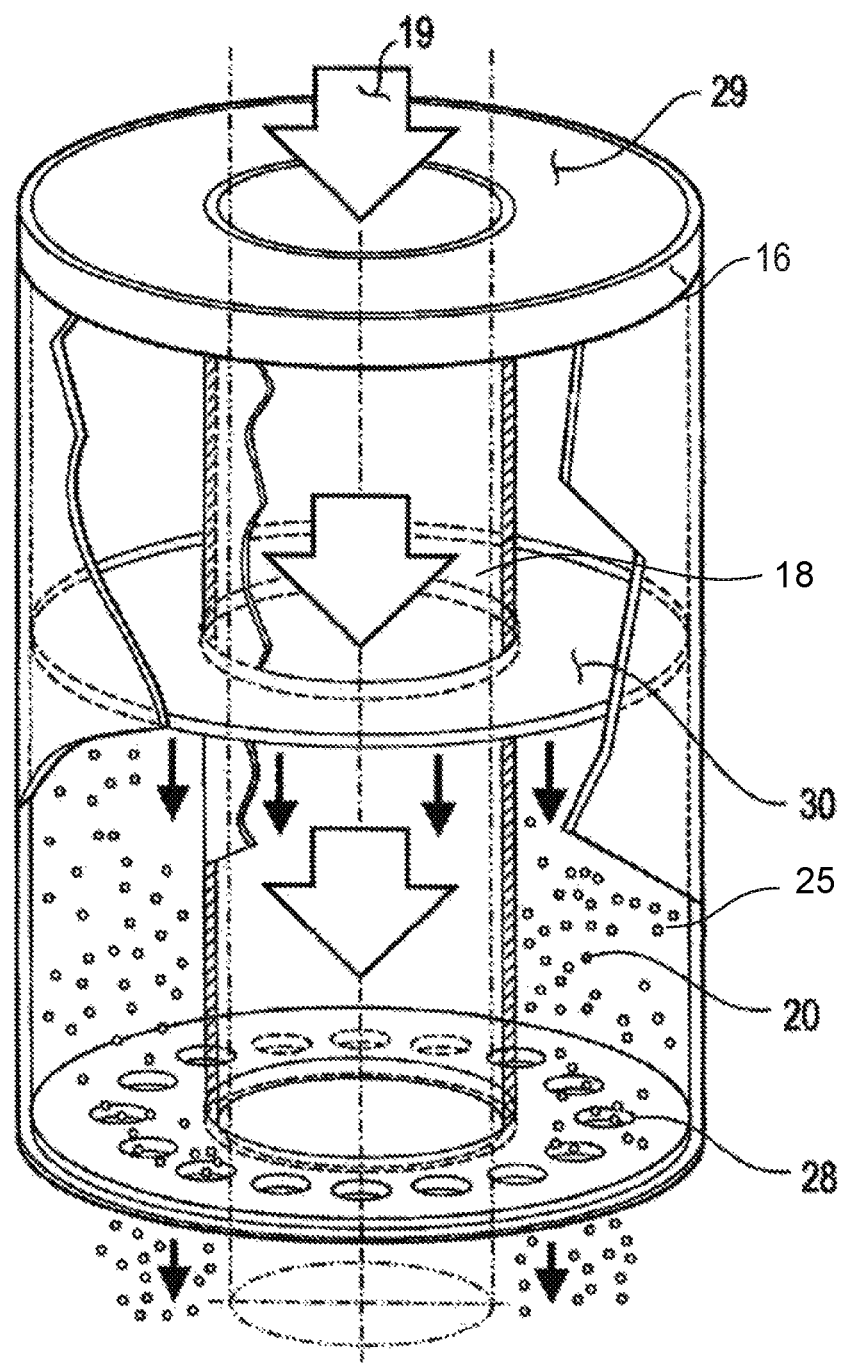
FIG. 15 shows an attachable tip with a magnetic piston.
Figure 16:
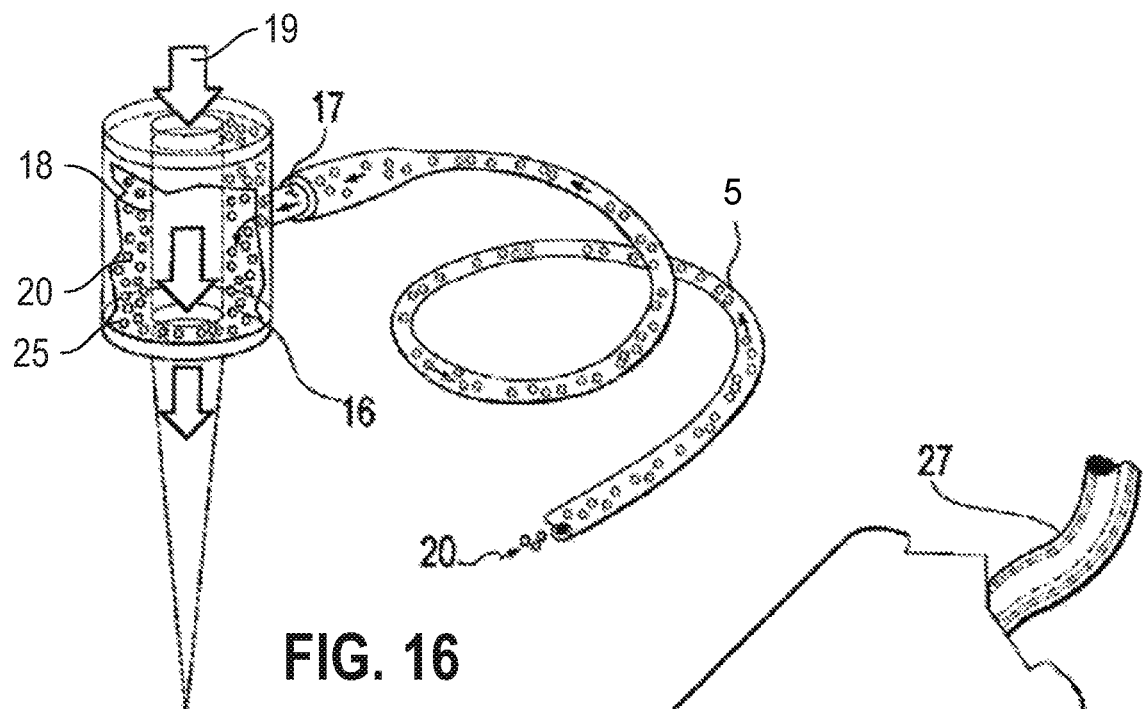
FIG. 16 shows a refillable attachable tip for a laser hand piece.
Figure 17:
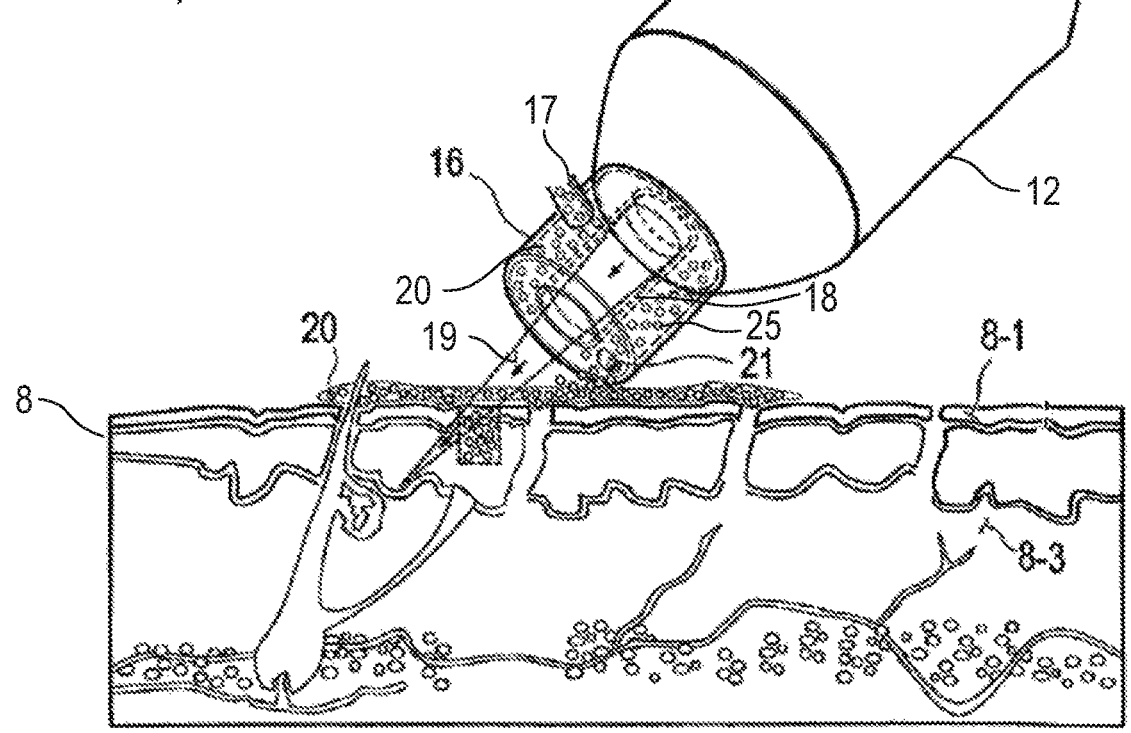
FIG. 17 shows a refillable attachable tip attached to a laser hand piece.

FIG. 13 shows an embodiment of an attachable tip in conjunction with a laser hand piece emitting a fractional laser beam. Fractional lasers are popular in dermatological and aesthetic fields. Some fractional laser systems contain hand piece attachable tips but fail to provide any therapeutic or cosmetic substances with it. The present invention demonstrates that a fractional laser hand piece can contain an attachable tip pre-filled with a medication, cosmetics or other substances that can be delivered during the lasering process. Attachable tip 16 has chamber 25 pre-filled with agent 20. Chamber 25 has at its lower end one or more windows 28 for placing chamber 25 in fluid communication with skin 8. Windows 28 traverse the inner and outer wall of chamber 25. Windows 28 can be in communication with one or more roller ball applicators 21 for rolling agent 20 onto skin 8. Windows 28, and the upper end of attachable tip 16, can be enclosed by removable seal 55. Before attaching attachable tip 16 to a laser hand piece, upper removable seal 55 has to be removed. In an alternative embodiment, seal 55 on the upper end of attachable tip 16 remains in place when attachable tip 16 is connected to a hand piece. In yet another embodiment, the upper end of attachable tip 16 is enclosed by a solid structure (e.g. upper wall). Removable seal 55 will be removed from the lower end of attachable tip 16 before the lasering process to permit agent 20 to flow from chamber 25 onto skin 8. Laser beam 19 can have a wavelength of around 1930 nm. Laser beam 19 can have a pulse energy around 5-20 mJ. Laser beam 19 can be a fractional $CO_2$ laser with a 10 micron wavelength and a pulse energy of 6-40 mJ. Laser beam 19 can be an Er:YSGG/Er:glass laser beam with a pulse energy of 2-35 mJ. Laser beam 19 can have a wavelength corresponding to a laser beam spot to produce an opening in the stratum corneum 8-1.

FIG. 14 shows an embodiment of an attachable tip in conjunction with laser hand piece 12. Attachable tip 16 has chamber 25 which contains agent 20. Located at the bottom of attachable tip 16 are one or more windows 28 for placing chamber 25 in fluid communication with the surface of skin 8. Attachable tip 16 is traversed lengthwise by hollow column 18 which is configured to permit laser beam 19 to traverse then length of attachable tip 16 unobstructed and contact skin 8. Hand piece 12 can produce laser beam 19, or laser beam 19 can be produced from a remote unit and transmitted to hand piece 12 through fiber optic conduction through connection 27. Alternatively, hand piece 12 can produce laser beam 19 and connection 27 can serve as a connection to a remote power source. Laser beam 19 can be a radio frequency (RF) laser beam or an intense pulsed light (IPL) laser beam. A pressure in chamber 25 can be maintained or produced by a squeezable bulb (not shown) of higher than an atmospheric pressure such that agent 19 will be forced out of attachable tip 16 through windows 28 during the laser delivering procedure. Laser beam 19 can be a diode laser with a wavelength in the range of 1,930 nm and pulse energy in the range of 3-40 mJ. The agent can be a myorelaxant compound. The agent can be botulinum toxin or a derivate of botulinum toxin.

FIG. 15 shows an embodiment of an attachable tip for use with a laser hand piece. Attachable tip 16 contains upper magnet 29 and lower magnet 30 which face one another with the same polarity so that magnetic forces create a pressure so that lower magnet 30 is forced towards the bottom of attachable tip 16 thereby placing agent 20 under pressure within chamber 25. Upper magnet 29 is attached to the wall of the attachable tip 16 and is used to attach attachable tip 16 to a hand piece by magnetic force. Lower magnet 30 is movable within attachable tip 16 and forms a seal with the inner walls of attachable tip 16 so that agent 20 can be contained within chamber 25 under pressure. Lower magnet 30 is pushed by magnetic forces from upper magnet 29 in the direction of attachable tip windows 28 thereby squeezing agent 20 out through windows 28 onto a laser treated surface (e.g. the skin of a subject). Attachable tip 16 contains hollow column 18 which permits laser beam 19 to traverse the length of attachable tip 16 unobstructed. Windows 28 can be sealed by a removable seal to prevent agent 20 from escaping until the release of agent 20 onto the surface of the skin is desired. Laser beam 19 can be a 1,930 nm laser beam. Agent 20 can be selected one or more agents selected from the group consisting of: a vaccine; antibody; long term release liposome; chemotherapeutic drug; and a combination thereof.

FIGS. 16 and 17 show an embodiment for an attachable tip that permits the refilling of agents during operation of a laser hand piece. Attachable tip 16 has chamber 25 for containing one or more agents 20. Attachable tip 16 has connector 17 which traverses the wall of attachable tip 16 and places chamber 25 in fluid communication with a suitable agent loading device. Agents can be loaded into chamber 25 through connector 17 via hollow conduit 5. Conduit 5 can be a tube or pipe of suitable material, such as, for example, vinyl, plastic, or polyethylene. Attachable tip 16 has hollow column 18 which traverses the length of attachable tip 16 and forms a path through which laser beam 19 can traverse the length of attachable tip 16 unobstructed. Laser beam 19 can be from a diode laser at 1,930 nm. Attachable tip 16 has one or more windows (not pictured) on its lower surface to permit agent 20 to flow from chamber 25 onto the surface of the skin of subject. These windows can be in fluid communication with one or more roller balls 21 for rolling agent 20 onto the skin of a subject. In practice, chamber 25 can be pre-loaded with agent 20, loaded through connector 17, or a combination thereof. Chamber 25 can be filled with agent 20 while laser beam 19 is applied to skin 8. Conduit 5 can be attached to a container (e.g. drug container, vial, IV bag, or syringe). Chamber 25 can be loaded before or during the application of laser beam 19. One skilled in the art will recognize that loading chamber 25 through connector 17 can provide a number of benefits. First, chamber 25 can be replenished with agent 20 should agent 20 be depleted during the lasering process. Second, other agents can be combined with agents already present in chamber 25. Third, a solid (e.g. lyophilized, preserved agent) can be contained within chamber 25, and then solubilized through the introduction of a suitable liquid when the application of agent 20 is desired. This permits agent 20 to remain preserved until the moment of application. Fourth, agents can be provided sequentially, or in series, such as an anesthetic to reduce pain during lasering, followed by filling and/or skin rejuvenating agents, then an antibiotic to prevent infection of the treated area.

Figure 18:
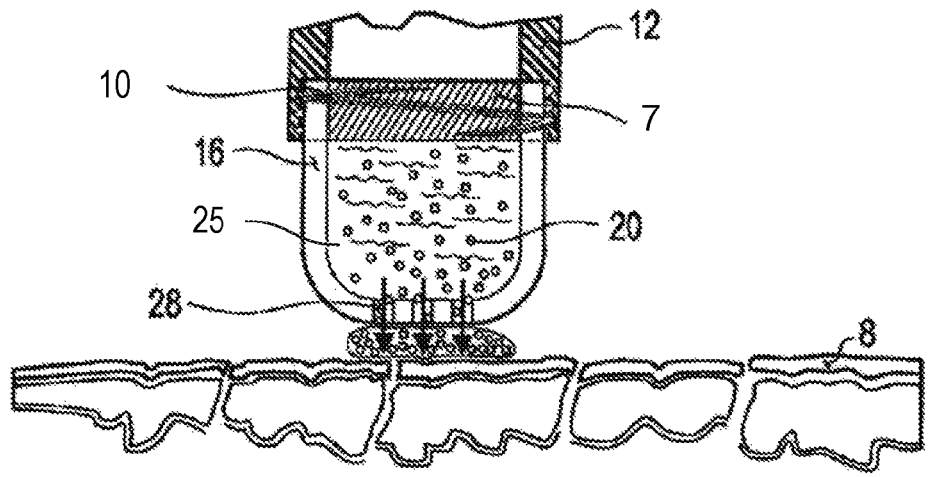
FIG. 18 shows an attachable tip for an ultrasound hand piece.
Figure 21:
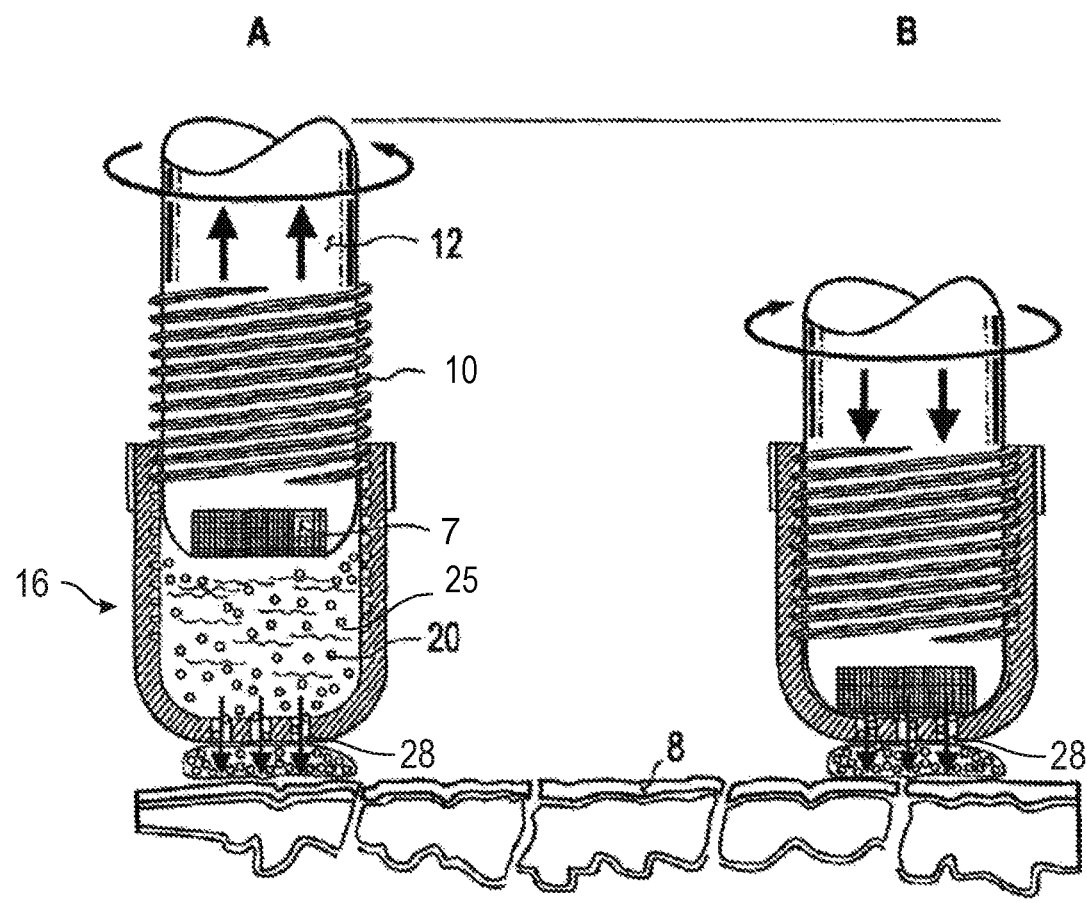
FIG. 21 shows a retractable attachable tip for an ultrasound hand piece.
Figure 24:
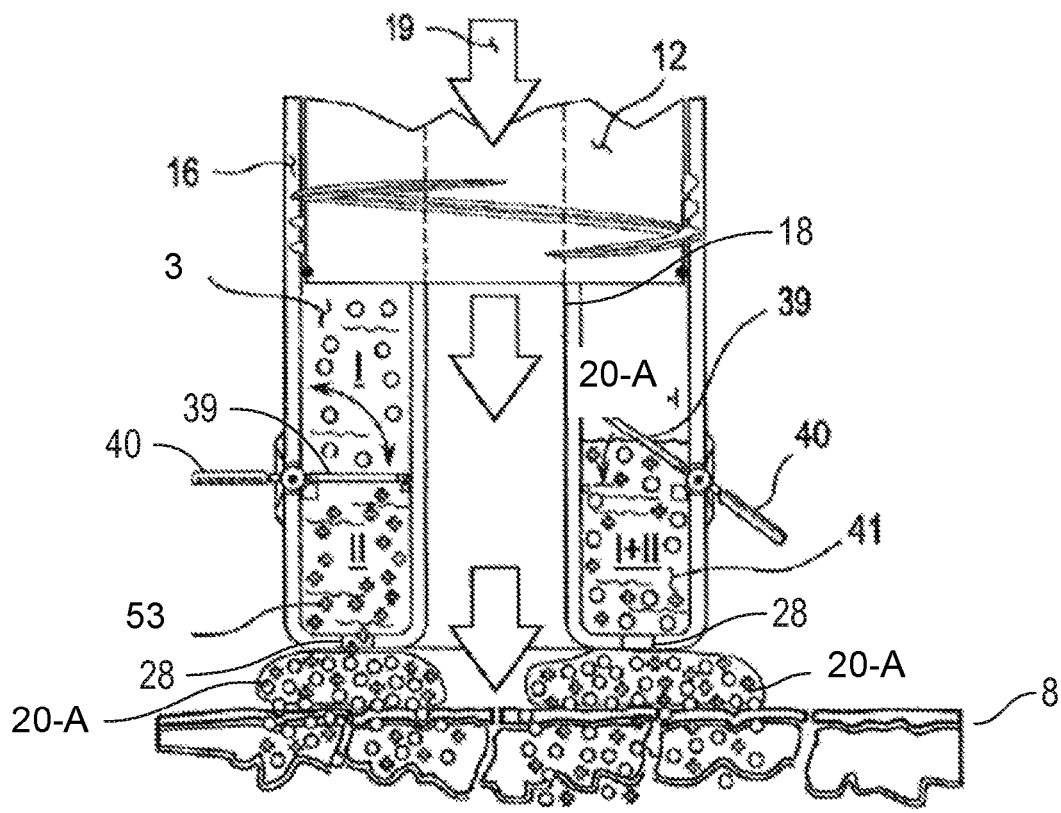
FIG. 24 shows an attachable tip for combining liquid and solid components.
Figure 25:
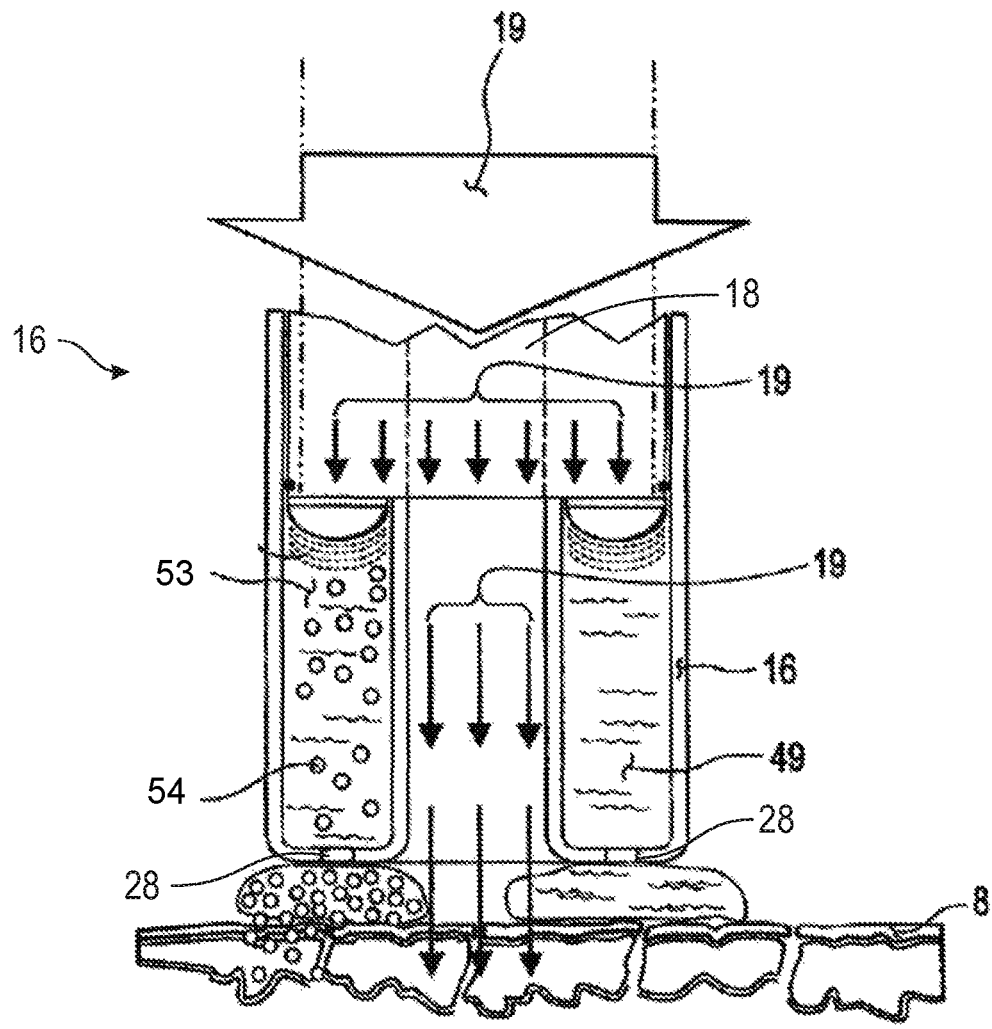
FIG. 25 shows an attachable tip configured to heat components within the chamber of the attachable tip.
Figure 26A:
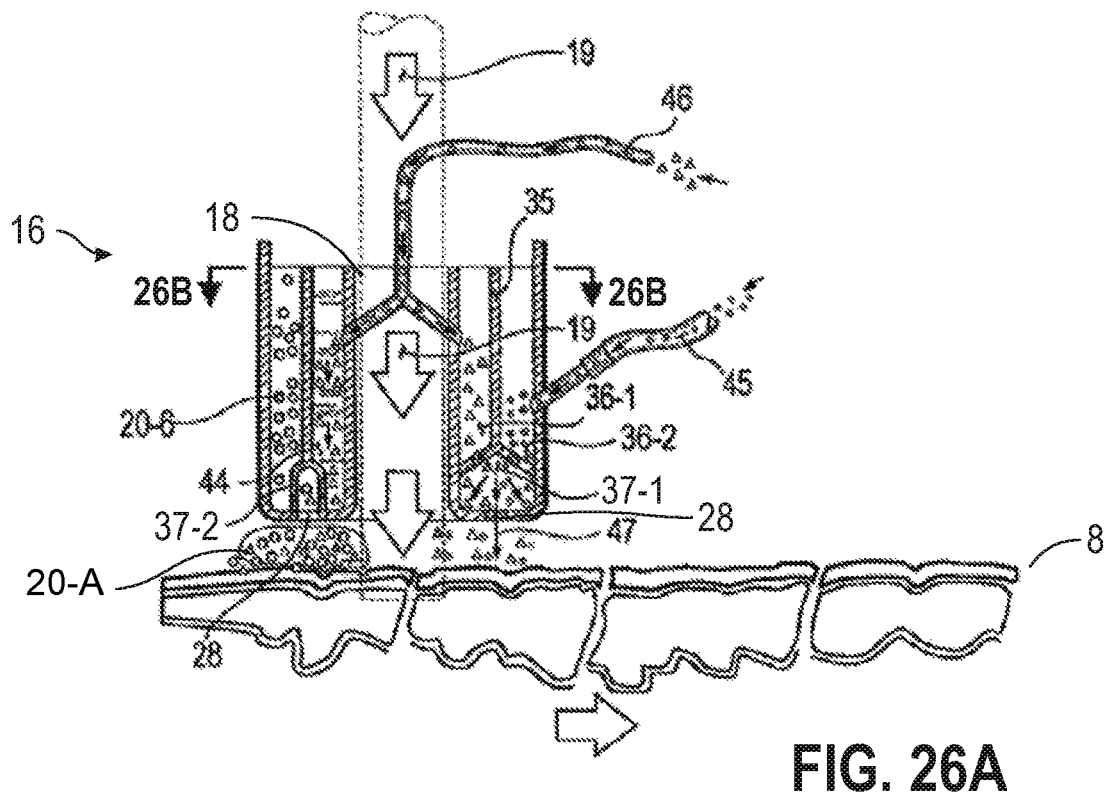
FIG. 26A shows a multi-chamber attachable tip with air and water cooling features.
Figure 26B:
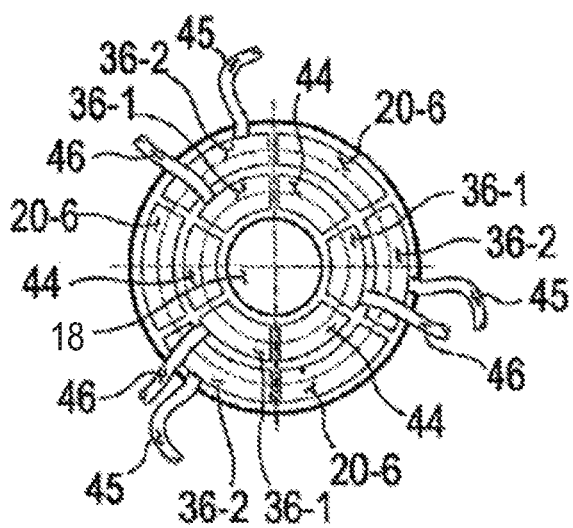
FIG. 26B shows a cross-sectional view of the multi-chamber attachable tip of FIG. 26A.

FIGS. 18 and 21 show an embodiment of an attachable tip for use with an ultrasound hand piece. Attachable tip 16 has a chamber 25 containing agent 20. The upper end of attachable tip 16 has threads which interact with threads 10 on hand piece 12 to connect attachable tip 16 to hand piece 12. Attachable tip 16 has one or more windows 28 for permitting agent 20 to escape from chamber 25 onto the surface of skin 8. Hand piece 12 has transducer 7 for producing ultrasound energy for conducting imaging on a subject. In practice, threads 10 can be engaged with the threads on hand piece 12 to advance hand piece 12 towards attachable tip 16. Advancing hand piece 12 towards attachable tip 16 can be used to decrease the volume of chamber 25 thereby creating pressure and forcing agent 20 out of chamber 25 through windows 28 onto the surface of skin 8.

Figure 19:
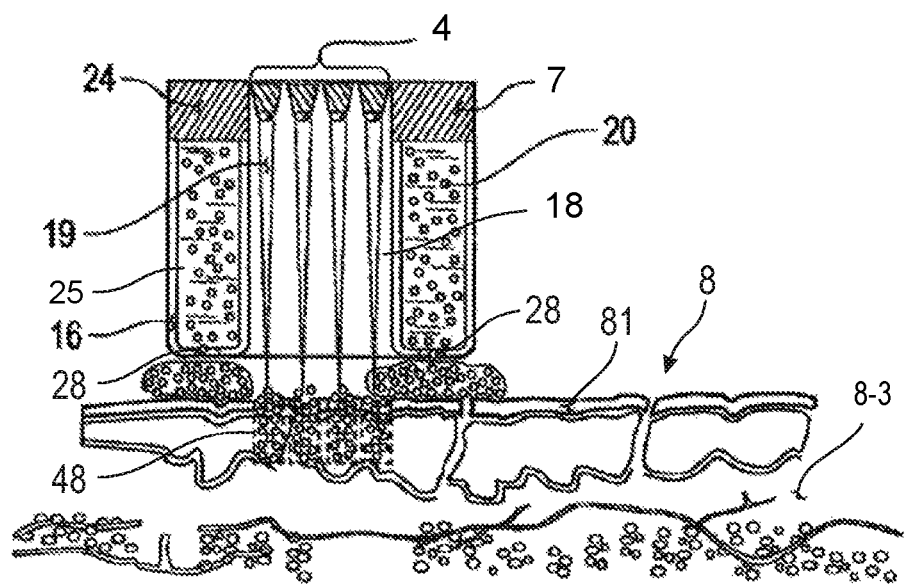
FIG. 19 shows an attachable tip for a hand piece with an ultrasonic transducer and internal diode lasers.
Figure 20:
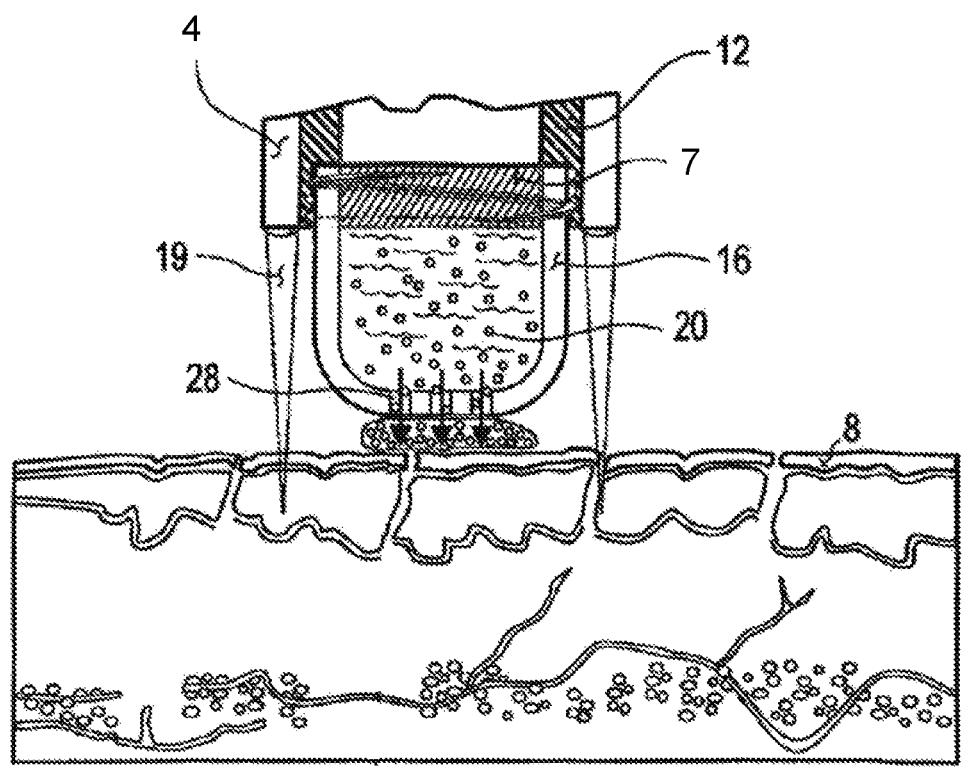
FIG. 20 shows an attachable tip for a hand piece with an internal ultrasonic transducer and external diode lasers.

FIG. 19 shows an attachable tip having both laser and ultrasound functions. Attachable tip 16 comprises transducer 7 and one or more laser diodes 4 for emitting one or more laser beams 19. Attachable tip 16 comprises chamber 25 for containing one or more agents 20. Attachable tip 16 terminates in one or more windows 28 for permitting agent(s) 20 to escape chamber 25 and contact skin 8. Attachable tip 16 has a circular cross section (not shown) such that chamber 25 forms an annular configuration that forms circular central column 18. Circular central column 18 permits laser beams 19 to traverse the length of attachable 16 unobstructed to contact skin 8. Laser beams 19 can be of the same or different wavelengths. Laser beams 19 can be of a wavelength sufficient to create holes 48 of a different depth and diameter in the skin's stratum corneum 8-1, and reticular dermis 8-3 thereby permitting agent(s) 20 to penetrate these structures in skin 8. Agent(s) 20 can be selected from the group consisting of: insulin; one or more insulin derivatives; and a combination thereof. In an alternative embodiment, transducer 7 and one or more laser diodes 4 form a portion of a hand piece that is separate from, and attachable to, attachable tip 16.

FIGS. 22 and 23 show attachable tips having multiple chambers for containing one or more agents separately. The attachable tips shown in FIGS. 22 and 23 can be used to store one or more agents separately, then combining them just before or simultaneously with the application of laser and/or ultrasound energy to the skin of a subject.

FIG. 22 shows an attachable tip having a pair of chambers D1 and D2. Chamber D1 is separated from chamber D2 by wall 35 on opposing sides of attachable tip 16. Wall 35 is interrupted by central column 18 which occupies the length of attachable tip 16 and forms a void through which one or more laser beams 19 from hand piece 12 can traverse the length of attachable tip 16 unobstructed to contact skin 8. Chamber D1 is depicted as containing a first one or more agents 20-1 and chamber D2 is depicted as containing a second one or more agents 20-2. Each of chambers D1 and D2 terminate in one or more windows 28 through which one or more agents 20-1 and 20-2 are permitted to escape the chambers to contact skin 8. When one or more agents 20-1 and 20-2 escape chambers D1 and D2, they combine to form composition 20-A on the surface of skin 8. Laser beam(s) 19 can be of a wavelength sufficient to create one or more holes 48 in skin 8 to permit agents 20-1, 20-2, and/or composition 20-A to penetrate skin 8. In an alternative embodiment, hand piece 12 has an ultrasound function that is provided by transducer 7 which forms an annular ring around the end of hand piece 12.

FIG. 23 shows an embodiment of an attachable tip having multiple chambers for containing one or more agents separately. This particular embodiment permits premixing of agents within the attachable tip prior to, or simultaneously with, the application of laser and/or ultrasound energy from an attached hand piece. Attachable tip 16 has chambers 36-1, 36-2 and 36-3 which form a number of concentric hemispheres along the length of attachable tip 16. Opposite chambers 36-1, 36-2 and 36-3 are a pair of chambers 36-4 and 36-5 which similarly form concentric hemispheres along the length of attachable tip 16. Chambers 36-1, 36-2 and 36-3 are separated from chambers 36-4 and 36-5 by wall 35. Wall 35 is interrupted by central column 18 which occupies the length of attachable tip 16 and forms a void to permit one or more laser beams 19, from an attached hand piece, to traverse the length of attachable tip 16 unobstructed so as to contact skin 8. One or more agents 20-1, 20-2, 20-3, 20-4, and 20-5 are contained individually in chambers 36-1, 36-2, 36-3, 36-4, and 36-5. A pair of mixing chambers 38-1 and 38-2 are provided at the lower portion of each set of concentric hemispheric chambers. Mixing chamber 38-1 forms a void that connects each of chambers 36-1, 36-2, and 36-3 through one or more windows (not shown). Agents 20-1, 20-2, and 20-3, combine in mixing chamber 38-1 to form composition 37-1. Mixing chamber 38-2 forms a void that connects chambers 36-4 and 36-5 through one or more windows (not shown). Agents 20-4 and 20-5 combine in mixing chamber 38-2 to form composition 37-2. Before or during the application of laser and/or ultrasound energy, the windows in mixing chambers 38-1 and 38-2 can be opened to permit the agents in the respectively connected chambers to combine. Alternatively, the windows in mixing chambers 38-1 and 38-2 are configured as open ports which permit the free mixing of agents without the need for opening the windows. Mixing chambers 38-1 and 38-2 each contain one or more windows 28 for permitting compositions 37-1 and 37-2 to escape and flow onto the surface of skin 8. Application of one or more laser beams 19 onto skin 8 can create one or more openings in skin 8 thereby permitting compositions 37-1 and 37-2 to permeate skin 8. Mixing chambers 38-1 and 38-2 can be used for combining hydrophobic components with water solutions, or to mix biologics with drugs like cytokines, stem cells, cell factors, HLA, PRP, or to mix hair coloring components after the laser bleaching of hairs, etc.

FIG. 24 shows an embodiment of an attachable tip having a chamber that is divided into a sub-chamber by a valve. Opening of the valve permits agents to be mixed prior to the application of laser and/or ultrasound energy from an attached hand piece. As shown in FIG. 24, attachable tip 16 is connected to hand piece 12 by interaction of threads. Chambers of attachable tip 16 in this embodiment are separated into two or more sub-chambers by valve 39. Valve 39 separates a lower portion of the chamber that is pre-filled with a solid state agent 53 from the upper part of the chamber that is pre-filled with fluid 3. When switch 40 opens valve 39, fluid 3 goes down through solid state agent 53 in the lower chamber thereby providing mixture 20-A for the delivery to the surface or cavity of the skin 8 through one or more windows 28. Attachable tip 16 can have an annular cross-section with column 18 forming a cylindrical void running the length of attachable tip 16 and forming a void through which one or more laser beams 19 can pass unobstructed onto the surface of skin 8. Laser beam(s) 19 can be of a wavelength, intensity and duration suitable for creating one or more openings in skin 8 to permit mixture 20-A to permeate skin 8. Laser beam(s) 19 can be from a diode laser with wavelength of 1,930 nm and pulse energy 6-12 mJ. Solid state agent 53 can be, for example a lyophilized, or otherwise preserved, drug or biologic. Solid state agent 53 can be a lyophilized vaccine, monoclonal antibody and/or fragment thereof. Solid state agent 53 can be Bevacizunab, Ramibizutab, Transtuzumab, TherCIM, Cetuximab, Infliximab, a cytokine, or stem cell factor. Fluid 3 can be lactated, water, Ringers solution, or sodium chloride (e.g. 0.9% solution.)

FIG. 25 shows an embodiment for an attachable tip with state-changing functionality. Attachable tip 16 forms a chamber in the shape of a double walled cylindrical annulus. The chamber is filled with solid state agent 53 and light electromagnetic energy absorbing particles 54. Particles 54 can be of micro or nanosize. When a laser hand piece is connected to attachable tip 16 and in operation to deliver one or more beams 19 to skin 8, it simultaneously passes through central column 18 and the chamber. Solid state agent 53 scatters energy in the chamber which is absorbed by particles 54 thereby raising the temperature in the chamber and transferring heat to surrounding solid state agent 53. This increase in heat causes a melting and transition of solid state agent 53 into liquid state 49. Liquid state 49 is permitted to escape from the chamber through one or more windows 28 and onto skin 8. Laser beam(s) 19 can be of a wavelength, duration and intensity sufficient to create openings in skin 8 thereby permitting liquid state 49 to permeate skin 8.

FIG. 26 shows an embodiment of an attachable tip having cooling, mixing and aerosol-forming functions. Attachable tip 16 has a plurality of chambers 20-6 for containing one or more agents. Chambers 36-1 and 44 contain cooled fluid that is received from conduits 46. Chambers 36-2 contain cooled gas that is received from gas conduits 45. Chambers 20-6 and 44 are in fluid communication with mixing chamber 37-2 through one or more windows (not shown) to permit one or more agents from chamber 20-6 to combine with cooled fluid from chamber 44 to form composition 20-A. Composition 20-A is permitted to exit mixing chamber 37-2 through one or more windows 28. Chambers 36-1 and 36-2 are in fluid communication with mixing chamber 37-1 through one or more windows (not shown) to permit cooled gas from chamber 36-2 to combine with cooled fluid from chamber 36-1 to form aerosol 47. Aerosol 47 is permitted to escape mixing chamber 37-1 through one or more windows 28. Attachable tip 16 has within its center hollow column 18 for permitting one or more laser beams 19 to pass unobstructed from a hand piece through the length of attachable tip 16 and onto skin 8. In operation, a cooled fluid is delivered into chambers 44 and 36-1 by conduits 46. Cooled air is simultaneously delivered to chambers 36-2 by conduits 45. The introduction of the cooled fluid to chamber 44 results in the formation of a composition 20-A as one or more agents from chamber 20-6 combine cooled fluid from chamber 44 in mixing chamber 37-2. The introduction of the cooled fluid to chamber 36-1 and cooled gas to chamber 36-2 results in the formation of aerosol 47 as the cooled fluid and cooled gas combine in mixing chamber 37-1. Composition 20-A and aerosol 47 exit windows 28 and contact skin 8 as one or more laser beams 19 are applied to skin 8. Thus, attachable tip 16 provides for the simultaneous application of a cooled therapeutic and/or cosmetic agent (i.e. composition 20-A) and a cooling aerosol (i.e. aerosol 47) to provide a more soothing application of laser energy to the skin of a subject. Composition 20-A and aerosol 47 can be applied to skin 8 before, after and/or simultaneously with the application of laser beam(s) 19 to skin 8. The cooled fluid can be water or a saline solution. The cooled gas can be air, nitrogen, or carbon dioxide. The fluid in this embodiment can be water, saline, lactate solution, or a combination thereof.

FIGS. 4A, 4B, and 4C show embodiments for an attachable tip. Each of the depicted attachable tips can contain one or more chambers for containing one or more agents in each elongated portion of the attachable tips. In the embodiment of the attachable tip of FIG. 4B, one or more laser beams 19 pass through a column in the middle elongated portion. In an embodiment of the attachable tip of FIG. 4A, laser beam(s) 19 pass through a column between a pair of elongated portions. The elongated portions of the depicted attachable tips can form a standoff for focusing laser beam(s) 19 onto the skin of a subject with the attachable tips are contacted with the skin of a subject. Thus, the length of the attachable tip can correspond to the focal point of laser beam(s) 19 as produced by directing lenses. Agents are permitted to escape the chambers from windows 41, 42 and 43. The chambers can contain different agents which can be applied right before, after and during laser action depending on the arrangement of the agents in the chambers and the direction in which the attachable tip is directed during the application of laser beam(s) 19. For example, for the dual standoff attachable tip of FIG. 4A, the chamber with window 42 can contain an anesthetic and the chamber with window 41 can be a therapeutic or skin care agent for skin treatment. Thus, by moving such an attachable tip in a direction with chamber of window 42 leading the movement, an aesthetic can be applied prior to the application of laser beam(s) 19 and followed by the application of a therapeutic or skin care agent from the trailing chamber with window 41. Similarly, the attachable tip of FIG. 4B can contain three separate agents that are applied before (window 41), during (window 43), and after (window 44) laser action by moving the tip in a direction with the chamber of window 41 leading the motion. Window 43 can be on one or both sides of hollow a central column which permits laser beam(s) 19 to exit the attachable tip. The attachable tips have a portion for connecting to a laser hand piece.

Figure 5:
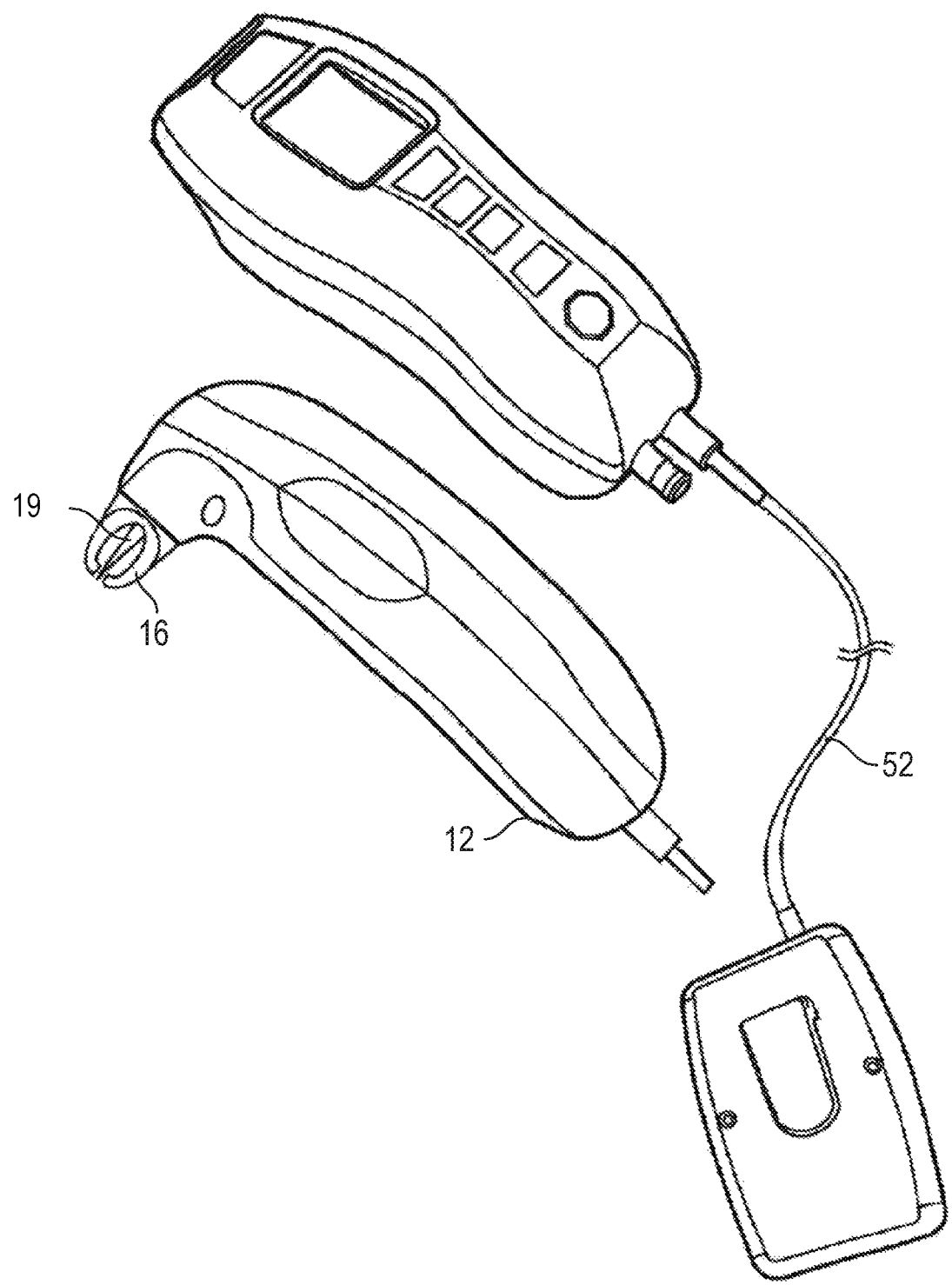
FIG. 5 shows a battery operated laser hand piece with an internal scanner and attachable tip.

FIG. 5 shows a laser hand piece with a scanner. Laser beam(s) 19 can be configured to produce a line of laser damages on a subject's skin. Laser beam(s) 19 can be produced by a more powerful laser module and used for treatment of large areas of skin. In order to produce a uniform delivery of an agent, attachable tip 16 can be replaced with an applicator in the form of a cylindrical roller. Alternatively, attachable tip 16 can contain a roller ball for applying an agent contained within a chamber in attachable tip 16. To provide an energy source to the laser, a rechargeable battery can be attached to the laser by cable 52. The battery can be clipped to the waist belt or be carried in a pocket. This system is also designed to deliver skin surface cooling. In preferred embodiments the surface cooling is provided with a flow of cold air. The cold air in preferred embodiments is at a temperature of about 0 to 3° C. and may be provided with a commercial, off-the-shelf air-cooling unit or with a simpler unit consisting of a blower unit, an accumulator and a tube coiled in an ice water bath.

The attachable tips disclosed herein can be adopted to be attached to the hand pieces of stationary medical and cosmetic lasers which are commercially available or already being used in practice. The attachable tips disclosed herein can be used with skin electroporation systems. In such case, damage of skin is produced by electrical energy and not light as in case of a laser.

The attachable tips disclosed herein can be attached to a hand piece by means of threads, magnets, interlocking male and female pieces, sliding dovetail configurations, and the like. Each of the attachable tips disclosed herein can be combined with hand pieces that deliver: laser energy; intensive pulse light (IPL) energy; ultrasound energy; radio frequency (RF) energy; microwave energy; light emitting diode energy; x-rays; ionizing radiation; and electron beams. The hand piece can be an ultrasound hand piece. The hand piece can be an electroporation device. The hand piece can be a device for emitting ionizing radiation, such as, for example, a device used in connection with radiation therapy of cancer. The hand piece can be a laser device, including, but not limited to a device having a laser selected from the group consisting of: Er:YAG; Er:YSSG; diode laser; solid state laser; excimere laser; $CO^2$ laser; CO laser; fiber laser; and a combination thereof.

Laser hand pieces for use with the invention can emit a laser wavelength ranging from 100 to 10,000 nm. The laser wavelength can be, +/−50 nm, 190 nm, 530 nm, 640 nm, 800 nm, 1,000 nm, 1,350 nm, 1,550 nm, 1,930 nm, 2,700 nm, 3,000 nm, 10,000 nm, or a combination thereof. The laser wavelength can be 190 nm, 530 nm, 640 nm, 800 nm, 1,000 nm, 1,350 nm, 1,550 nm, 1,930 nm, 2,700 nm, 3,000 nm, 10,000 nm, or a combination thereof.

The attachable tips disclosed herein can be used to accomplish the delivery of one or more therapeutic and/or cosmetic agents. The agent can be a drug, biologic, or cosmetic agent. The drug can be an antibody, gene, vaccine, antigenic peptide or protein, filling agent (e.g. hyaluronic acid), metal, small molecule, large molecule, or a combination thereof. The agent can be a vasodilator (e.g. minoxidil). The agent can be stem cell factors. The stem cell factors can be mesenchymal stem cell factors, including, but not limited to, the stem cell factors disclosed in US Patent Application Publication Nos. 2012/0201786 and 2016/0324898, the entire contents of which are incorporated by reference herein in their entirety. The agent can be a PCSK9 inhibitor (e.g. Praluent, Lucentis, Avasitin, or a combination thereof). The agent can be a protein kinase inhibitor. The agent can be a protein kinase antigen capable of producing antibodies against a protein kinase. The agent can be a combination of minoxidil, Wnt proteins, and one or more stem cell factors. The agent can be a combination of minoxidil, Wnt proteins, and one or more mesenchymal stem cell factors. The agents disclosed herein can be in the form of microparticles, nanoparticles, large particles, liposomes, microsomes, multiphase compositions. The agents can be an exosome. The agents can be an exosome secreted by a mesenchymal stem cell. The agents can be an exosome secreted by a mesenchymal stem cell grown under low oxygen conditions. The agent can be an analgesic, anesthetic, immunosuppressant, antibiotic, lubricant, coolant, dye, optical enhancer, energy absorber, energy dissipater, or combination thereof. The agent can be insulin or an insulin derivative. The agent can be botulinum toxin or a derivative thereof.

The agent can be a multiphase composition. Accordingly, the agent can be one or more of a liquid, solid phase (e.g. particle), gas, and gel. The agent can be a liquid gas and a fluid. The agent can be fluids of different viscosities. The agent can be a liquid gas and a solid phase. The agent can be a gel and a fluid. The agent can be a mixture of hydrophobic and hydrophilic liquids in a suspension.

FIG. 6, shows the system in operation with the hand piece being used to treat the face of a patient. In this embodiment a focused laser beam damages tiny volumes of skin tissue about 0.05×0.1 mm at the surface of the skin. Due to compact size of the device the procedure can be performed by a medical practitioner (e.g. doctor, nurse, etc.) or by the patient. The laser hand piece can have an internal scanner to provide laser damage at one position of the hand piece, also the beam shaping lenses can be designed in such a way to provide application of plurality of laser beams.

The above embodiments describe techniques for skin treatments based on the concept of the combination of a laser delivery system's hand piece and an agent-containing tip temporarily attached to each other in one unit. The laser beam produces damage to the skin and the applicator delivers an agent from the attachable tip to the damage zone. That combination provides a convenient way to deliver medical, cosmetic and/or skin care agents under the surface of the skin and thus improving the skin's appearance. It will be appreciated that this concept can be extended to other types of treatments including electrolysis units, for example.

A hand held laser with scanning system is used for large area skin treatment. For skin rejuvenation purposes attachable tips with vitamins and antioxidants, botulin toxin and its derivatives in the liquid form, cytokines and cell factors can be used. This combination is for large area skin rejuvenation including neo-collagen formation, sebaceous gland and bulge area stem cell mobilization can be used with delivery substances to regrow hairs.

Laser hand pieced for use with the invention can be single or dual wavelength with or without scanners. Laser hand pieces can be obtained from Dolleris Technology, nLight and Intezity Innovation, Coherent and IPG Photonics. Other laser hand piece suppliers include Palomar (Burlington, Mass.), Cynosure (Westford, Mass.), Candela (Wayland, Mass.), Sciton (Palo Alto, Calif.), Lumenis (Santa Clara, Calif.), Cutera (Brisbane, Calif.), Lutronic (Fremont, Calif.).

The reader should understand that the above specific embodiments of the present invention are merely examples and that many changes and modifications could be made without departing from the important concepts of the present invention.

The invention claimed is:

1. A tip for permitting an ultrasound handpiece to apply agents to the skin, comprising:
   a) a tip body adapted to connect to an ultrasound handpiece having a transducer;
   b) a chamber contained within said tip body, wherein said chamber is defined by a wall that is adapted to contain at least one agent; and
   c) at least one window in said wall;
   wherein (i) said at least one window is adapted to place said chamber in fluid communication with the skin of a patient when said tip is contacted with said skin, (ii) said wall is contiguous and free of openings with the exception of said at least one window, and (iii) said tip body is adapted to surround said transducer when said tip body is connected to said ultrasound handpiece.

2. The tip of claim 1, wherein said tip body is adapted to detachably connect to said ultrasound handpiece.

3. The tip of claim 1, wherein said tip body has a circular cross-section.

4. The tip of claim 1, wherein said tip body is adapted to slidably connect to said transducer.

5. The tip of claim 1, wherein said tip body forms an annulus around said transducer when said tip body is connected to said ultrasound handpiece such that said chamber and said transducer are adapted to contact said skin simultaneously when said tip is contacted with said skin.

6. The tip of claim 1, wherein said chamber covers a terminal end of said transducer when said tip body is connected to said ultrasound handpiece.

7. The tip of claim 1, wherein said at least one window is capped with a removable seal.

8. The tip of claim 1, wherein said tip further comprises a roller ball adapted to roll said at least one agent onto said skin.

9. The tip of claim 1, wherein said wall is adapted to contain at least one of a cooling gel, lubricant, and ultrasound imaging agent.

10. The tip of claim 1, wherein said tip body is formed from a flexible material adapted to permit said tip to be squeezed and force said at least one agent from said chamber onto said skin through said at least one window.

11. The tip of claim 1, wherein said tip is adapted to permit ultrasound energy from said transducer to force said at least one agent from said chamber through said at least one window onto said skin when said tip body is connected to said ultrasound handpiece and said ultrasound handpiece is activated.

* * * * *